US012073223B1

(12) United States Patent
DeTolla et al.

(10) Patent No.: US 12,073,223 B1
(45) Date of Patent: Aug. 27, 2024

(54) APPARATUSES, COMPUTER-IMPLEMENTED METHODS, AND COMPUTER PROGRAM PRODUCTS FOR ACCURATE DATA CODE PROCESSING UTILIZING AUGMENTED DATA CODES

(71) Applicant: Optum, Inc., Minnetonka, MN (US)

(72) Inventors: Michael J. DeTolla, Bainbridge Island, WA (US); David J. Falk, Highland Park, NJ (US); Chad L. Hilton, Centerville, UT (US); Paul C. Van Fossan, Eden Prairie, MN (US); Kelly Hogan, Encinitas, CA (US); Troy C. Lacher, Franklin, TN (US); Mark L. Morsch, San Diego, CA (US)

(73) Assignee: Optum, Inc., Minnetonka, MN (US)

( * ) Notice: Subject to any disclaimer, the term of this patent is extended or adjusted under 35 U.S.C. 154(b) by 399 days.

(21) Appl. No.: 17/645,027

(22) Filed: Dec. 17, 2021

Related U.S. Application Data

(60) Provisional application No. 63/158,163, filed on Mar. 8, 2021.

(51) Int. Cl.
*G06F 9/38* (2018.01)
*G06F 16/35* (2019.01)
(Continued)

(52) U.S. Cl.
CPC .......... *G06F 9/3895* (2013.01); *G06F 16/353* (2019.01); *G16H 10/60* (2018.01); *G16H 40/20* (2018.01); *G16H 15/00* (2018.01)

(58) Field of Classification Search
CPC ............................... G06F 16/215; G06F 16/22
See application file for complete search history.

(56) References Cited

U.S. PATENT DOCUMENTS 4,491,725 A 1/1985 Pritchard
7,363,240 B1 4/2008 Armentano et al.
(Continued)

FOREIGN PATENT DOCUMENTS

WO WO-2019067627 A1 * 4/2019 ............. G08B 19/00

OTHER PUBLICATIONS

Doctor AI: Predicting Clinical Events via Recurrent Neural Networks (Year: 2006).*
(Continued)

*Primary Examiner* — Yuk Ting Choi
(74) *Attorney, Agent, or Firm* — ALSTON & BIRD LLP

(57) ABSTRACT

Embodiments of the present disclosure provide for improved determination of complexities associated with event data objects. Such complexity determinations may be identified based at least in part on complexity score(s) generated from any number of augmented event codes. Embodiments identify augmented event codes from any of a myriad of sources, including various service encodings and participant history profiles for particular event entities. The augmented event codes may be processed in a myriad of ways, utilizing the entirety and/or portions thereof, to further enhance the accuracy of the event complexity determined therefrom. Based at least in part on the accurately generated complexity determination(s), one or more prediction-based actions may be initiated that correspond to the particular complexity determination(s), for example such that only the correct prediction-based action is initiated based at least in part on such a determined event complexity.

20 Claims, 14 Drawing Sheets

(51) Int. Cl.
    *G16H 10/60*     (2018.01)
    *G16H 40/20*     (2018.01)
    *G16H 15/00*     (2018.01)

(56) References Cited

U.S. PATENT DOCUMENTS

| | | |
|---|---|---|
| 7,840,422 B1 | 11/2010 | Hail et al. |
| 7,979,289 B2 | 7/2011 | Callas |
| 8,326,653 B2 | 12/2012 | Gottlieb et al. |
| 8,688,607 B2 | 4/2014 | Pacha |
| 8,694,343 B2 | 4/2014 | Olaniyan |
| 10,552,576 B2 | 2/2020 | Campbell |
| 10,685,743 B2 | 6/2020 | Ginsburg et al. |
| 2004/0254816 A1 | 12/2004 | Myers |
| 2015/0310573 A1 | 10/2015 | Grant |
| 2016/0253461 A1 | 9/2016 | Sohr et al. |
| 2020/0176091 A1* | 6/2020 | Vanderhoef ............ G16H 50/30 707/737 |
| 2022/0027765 A1* | 1/2022 | Parrish ................... G06N 20/20 707/737 |
| 2022/0301031 A1* | 9/2022 | Iyer .................... G06Q 30/0623 707/737 |
| 2022/0335518 A1* | 10/2022 | Wellmann ............... G06F 40/20 707/737 |
| 2022/0391793 A1* | 12/2022 | Latimer .................. G06F 40/20 707/737 |

OTHER PUBLICATIONS

Hurley, Robert E. et al. "Emergency Room Use and Primary Care Case Management: Evidence From Four Medicaid Demonstration Programs," American Journal of Public Health, Jul. 1989, vol. 79, No. 7, pp. 843-846.

Yang, Jinhong et al. "Proof-of-Familiarity: A Privacy-Preserved Blockchain Scheme For Collaborative Medical Decision-Making," Applied Sciences, Apr. 1, 2019, vol. 9, No. 7:1370, pp. 1-24, DOI: 10.3390/app9071370.

* cited by examiner

APPARATUSES, COMPUTER-IMPLEMENTED METHODS, AND COMPUTER PROGRAM PRODUCTS FOR ACCURATE DATA CODE PROCESSING UTILIZING AUGMENTED DATA CODES

CROSS-REFERENCE TO RELATED APPLICATIONS

This application claims priority to U.S. Provisional Application No. 63/158,163, filed Mar. 8, 2021, titled "E/M Professional Analyzer," the contents of which are incorporated by reference herein in their entirety.

TECHNOLOGICAL FIELD

Embodiments of the present disclosure generally relate to data code processing for one or more determinations, and specifically to generating and/or processing a plurality of augmented data codes for more accurately performing one or more determinations based at least in part on such augmented data codes.

BACKGROUND

In various contexts, data systems receive a myriad of data codes, such as event codes, associated with a particular event for further processing. Such data codes may include subsets of data codes from various systems associated with various entities, each subset associated with different levels of trustworthiness and/or accuracy. Often, one or more of such subsets of data codes may not be trustworthy and/or accurate but need to be processed for any number of determinations, resulting in determinations that are neither trustworthy and/or accurate. Applicant has discovered problems with current implementations of data code processing for one or more determinations. Through applied effort, ingenuity, and innovation, Applicant has solved many of these identified problems by developing embodied in the present disclosure, which are described in detail below.

BRIEF SUMMARY

In general, embodiments of the present disclosure provided herein provide accurate data code processing utilizing augmented data codes. Other implementations for accurate data code processing utilizing augmented data codes will be, or will become, apparent to one with skill in the art upon examination of the following figures and detailed description. It is intended that all such additional implementations be included within this description be within the scope of the disclosure, and be protected by the following claims.

In accordance with one aspect of the present disclosure, a computer-implemented method for determining a predicted risk-aware complexity determination for an event data object is provided. The computer-implemented method may be performed on any of a myriad of computing devices in hardware, software, firmware, and/or a combination thereof, as described herein. In one example implementation of the computer-implemented method, the example computer-implemented method includes identifying, using a processor, a plurality of augmented event codes for the event data object. The example computer-implemented method further includes for each augmented event code, determining, using the processor, a code-wise risk score that describes a measure of contribution of the augmented event code to an event complexity of the event data object, and determining, using the processor, a code-wise complexity designation that describes whether the augmented event code is associated with a predefined complexity category. The example computer-implemented method further includes determining, using the processor, a risk-based complexity score for the event data object, where: (i) the risk-based complexity score is determined based at least in part on each code-wise risk score for an intensive risk subset of the plurality of augmented event codes, and (ii) the intensive risk subset is determined based at least in part on each code-wise risk score for the plurality of augmented event codes. The example computer-implemented method further includes determining, using the processor, a category-based complexity score for the event data object based at least in part on each code-wise complexity designation for the plurality of augmented event codes. The example computer-implemented method further includes generating the predicted risk-aware complexity determination based at least in part on the risk-based complexity score and the category-based complexity score. The example computer-implemented method further includes performing one or more prediction-based actions based at least in part on the predicted risk-aware complexity determination.

Additionally or alternatively, in some embodiments of the example computer-implemented method, the plurality of augmented event codes comprise one or more primary event codes associated with a primary service encoding for the event data object.

Additionally or alternatively, in some embodiments of the example computer-implemented method, the plurality of augmented event codes comprise one or more historical event codes associated with a participant history profile for the event data object.

Additionally or alternatively, in some such embodiments of the example computer-implemented method, the one or more historical event codes comprise each event code associated with the participant history profile Additionally or alternatively, in some such embodiments of the example computer-implemented method, the one or more historical event codes comprise a selected subset of event codes associated with the participant history profile that are also associated with a selected time interval for the event data object.

Additionally or alternatively, in some embodiments of the example computer-implemented method, the one or more historical event codes comprise each event code associated with the participant history profile that are also associated with a subject matter designation of the event data object.

Additionally or alternatively, in some embodiments of the example computer-implemented method, the intensive risk subset comprises a defined-size subset of the plurality of augmented event codes having highest category-based complexity scores among the plurality of augmented event codes.

Additionally or alternatively, in some embodiments of the example computer-implemented method, determining the category-based complexity score includes determining a selected subset of the plurality of augmented event codes having affirmative code-wise complexity designations; determining a size of the selected subset; and determining the category-based complexity score based at least in part on whether the size satisfies a size threshold.

Additionally or alternatively, in some embodiments of the example computer-implemented method, the event data object fails to satisfy one or more initial complexity conditions.

In accordance with another aspect of the present disclosure, an apparatus for determining a predicted risk-aware complexity determination for an event data object is provided. In some example embodiments of the apparatus, the example apparatus includes at least one processor and at least one memory having computer-coded instructions stored thereon. The computer-coded instructions, in execution with the at least one processor, cause the apparatus to perform any one of the example computer-implemented methods described herein. In some other embodiments of the apparatus, the example apparatus includes means for performing each step of any one of the computer-implemented methods described herein.

In accordance with yet another aspect of the present disclosure, a computer program product for determining a predicted risk-aware complexity determination for an event data object is provided. In some example embodiments of the computer program product, the example computer program product includes at least one non-transitory computer-readable storage medium having computer program code stored thereon that, in execution with at least one processor, is configured for performing any one of the example computer-implemented methods described herein.

BRIEF DESCRIPTION OF THE DRAWINGS

Figure 1:
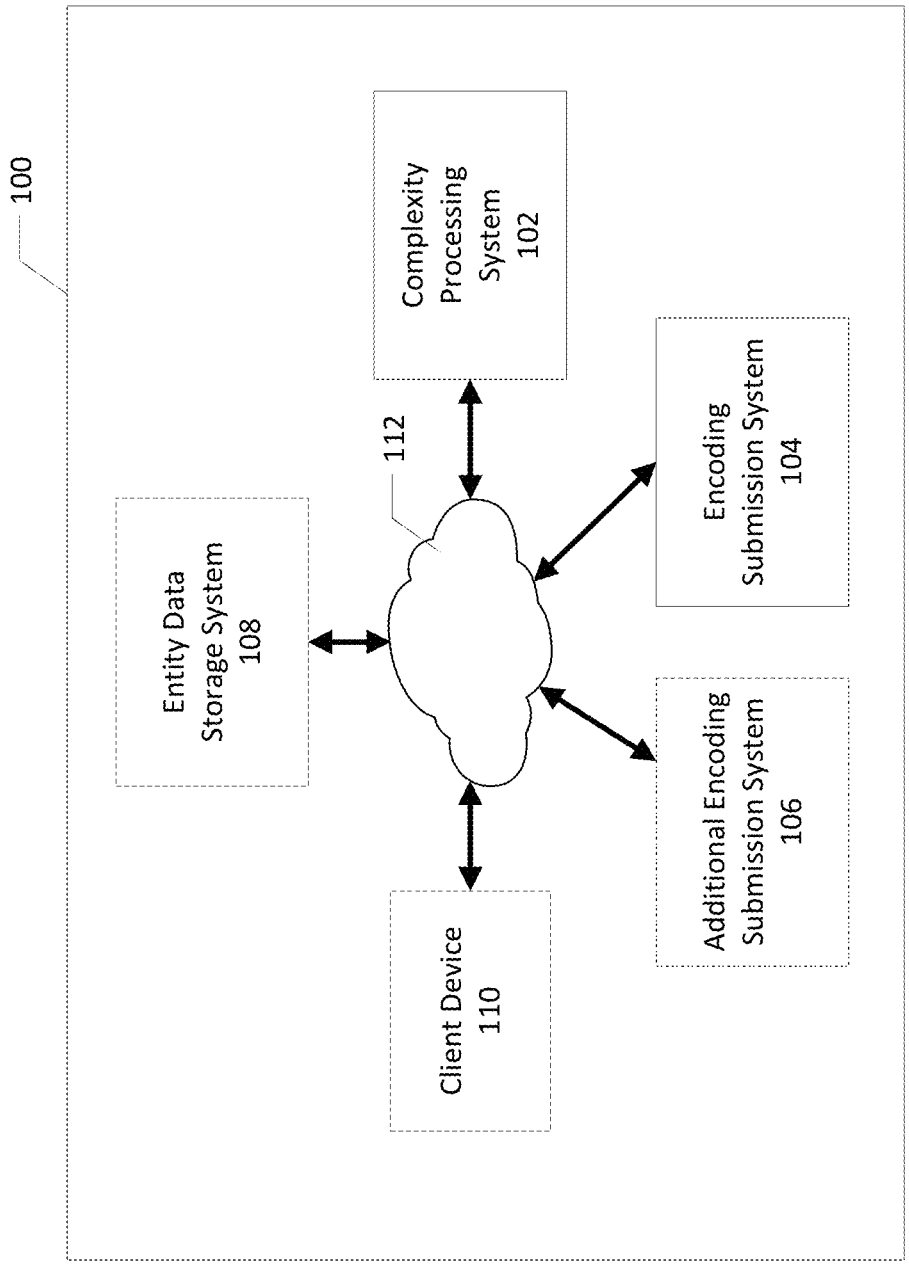
Figure 2:
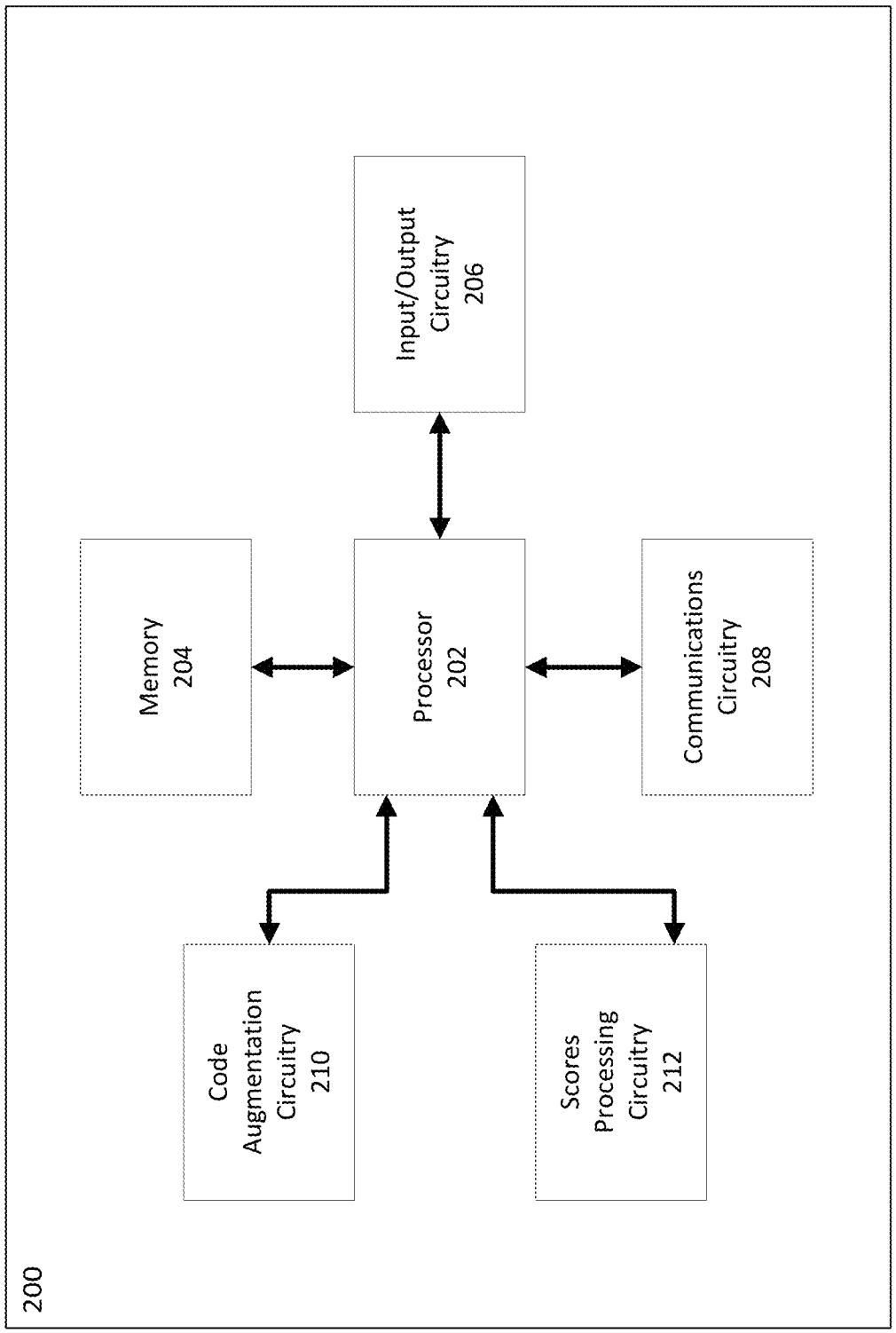
Figure 3:
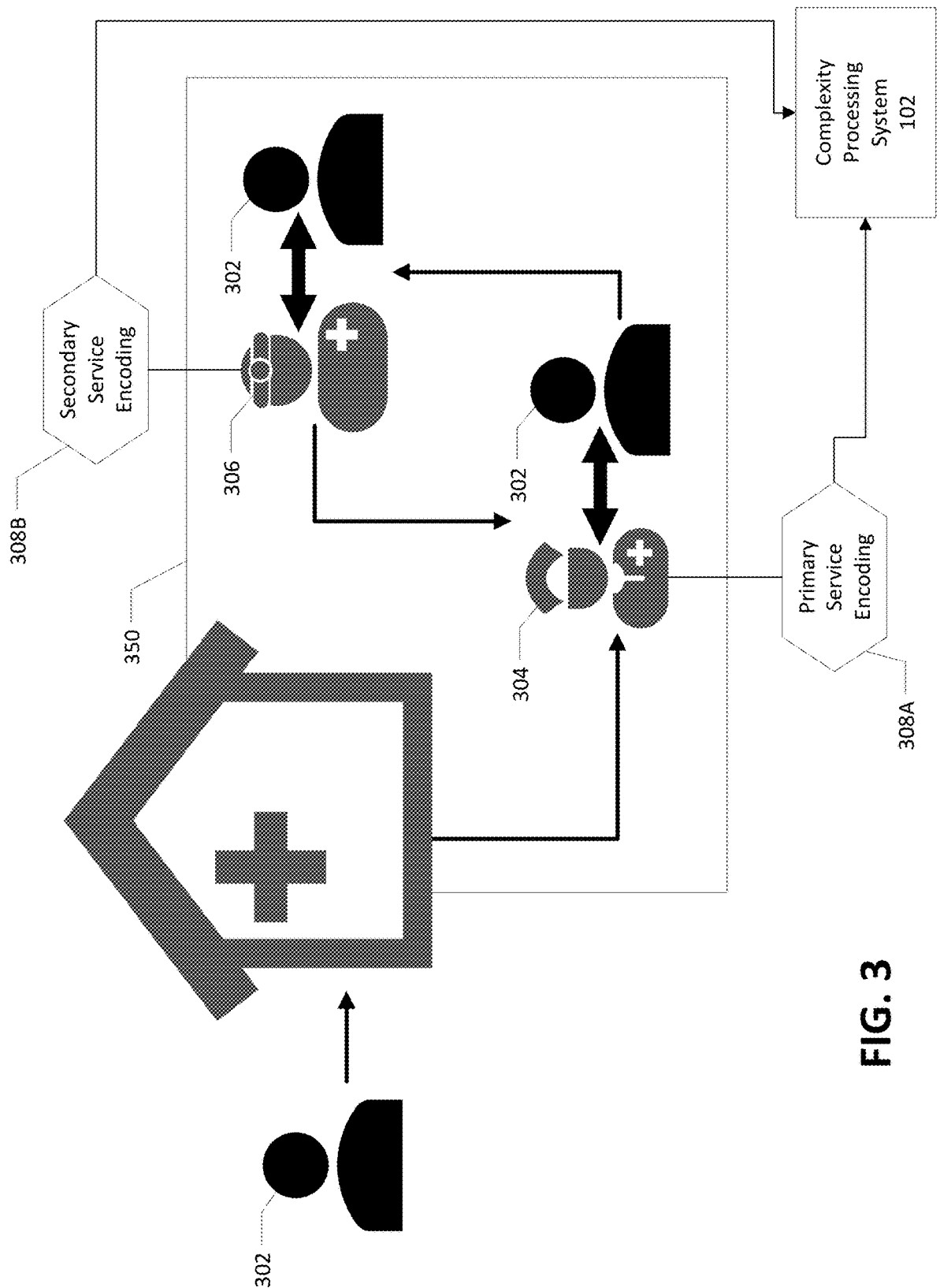
Figure 4:
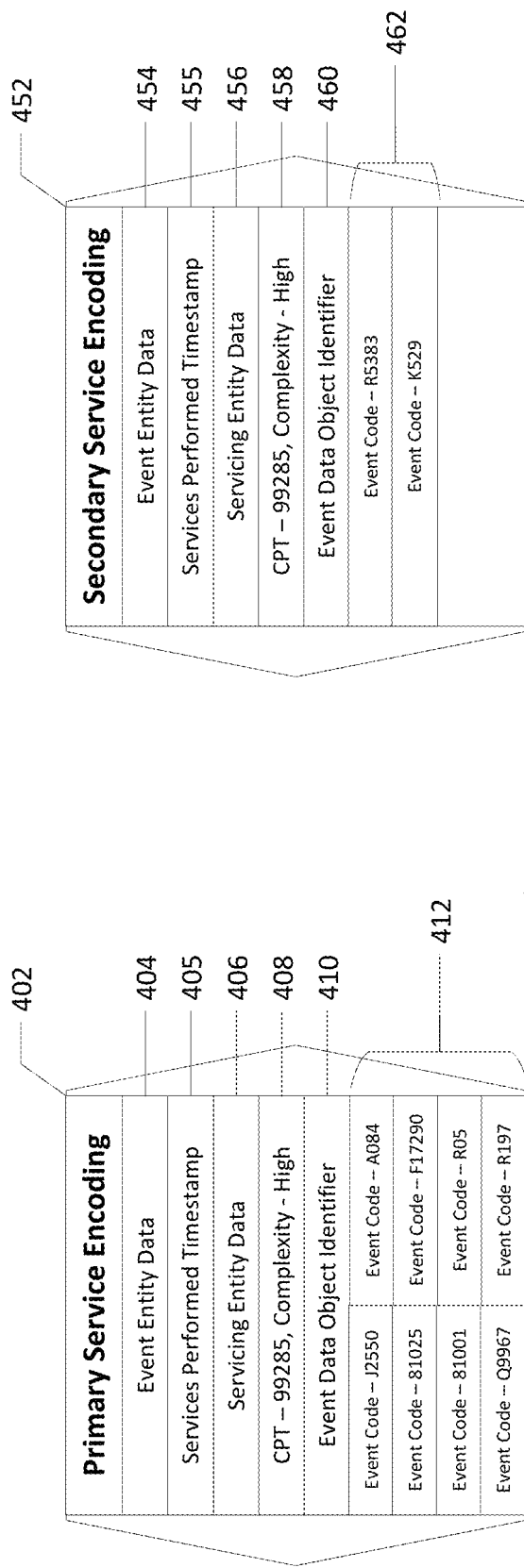
Figure 5:
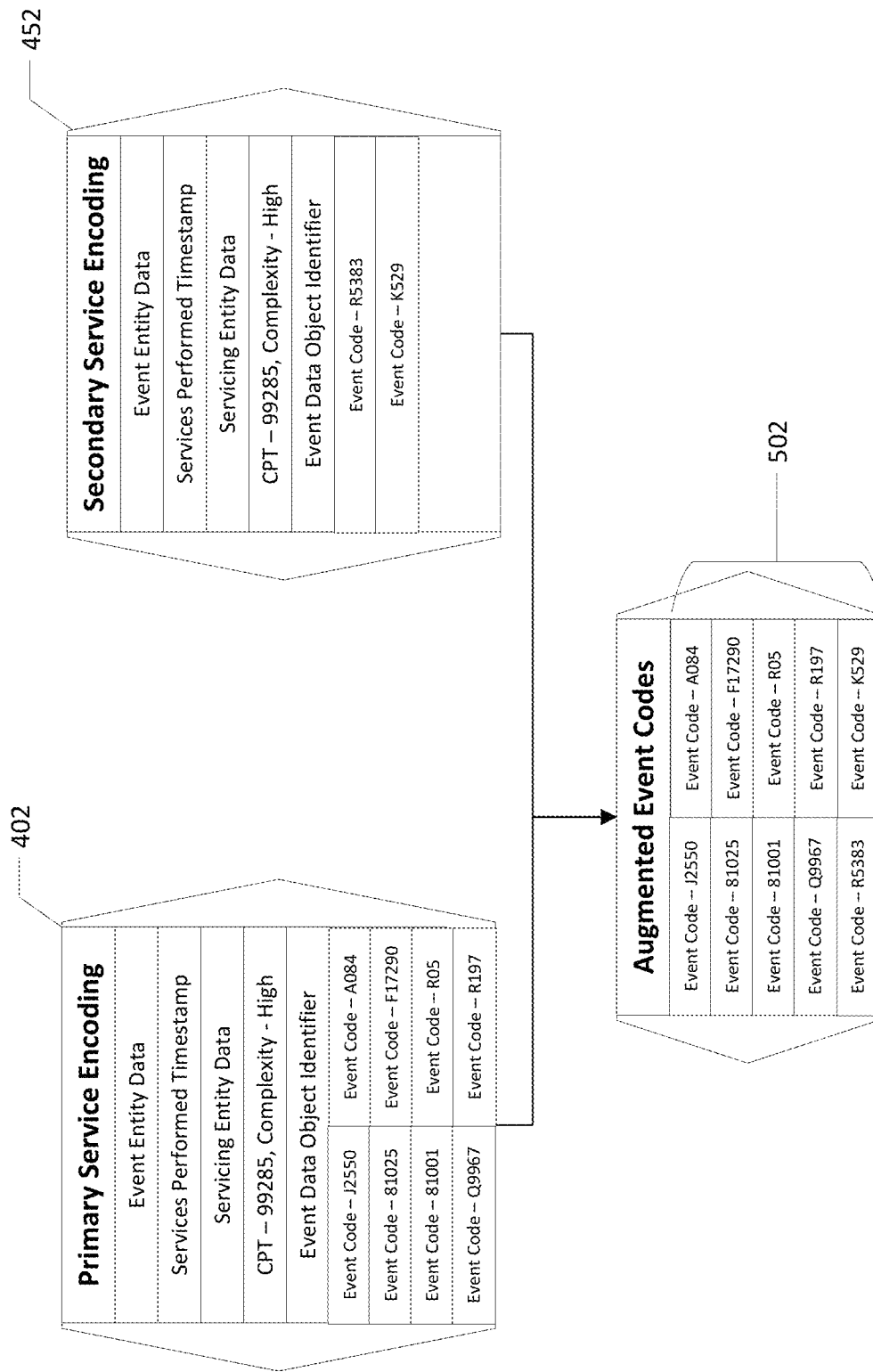
Figure 6:
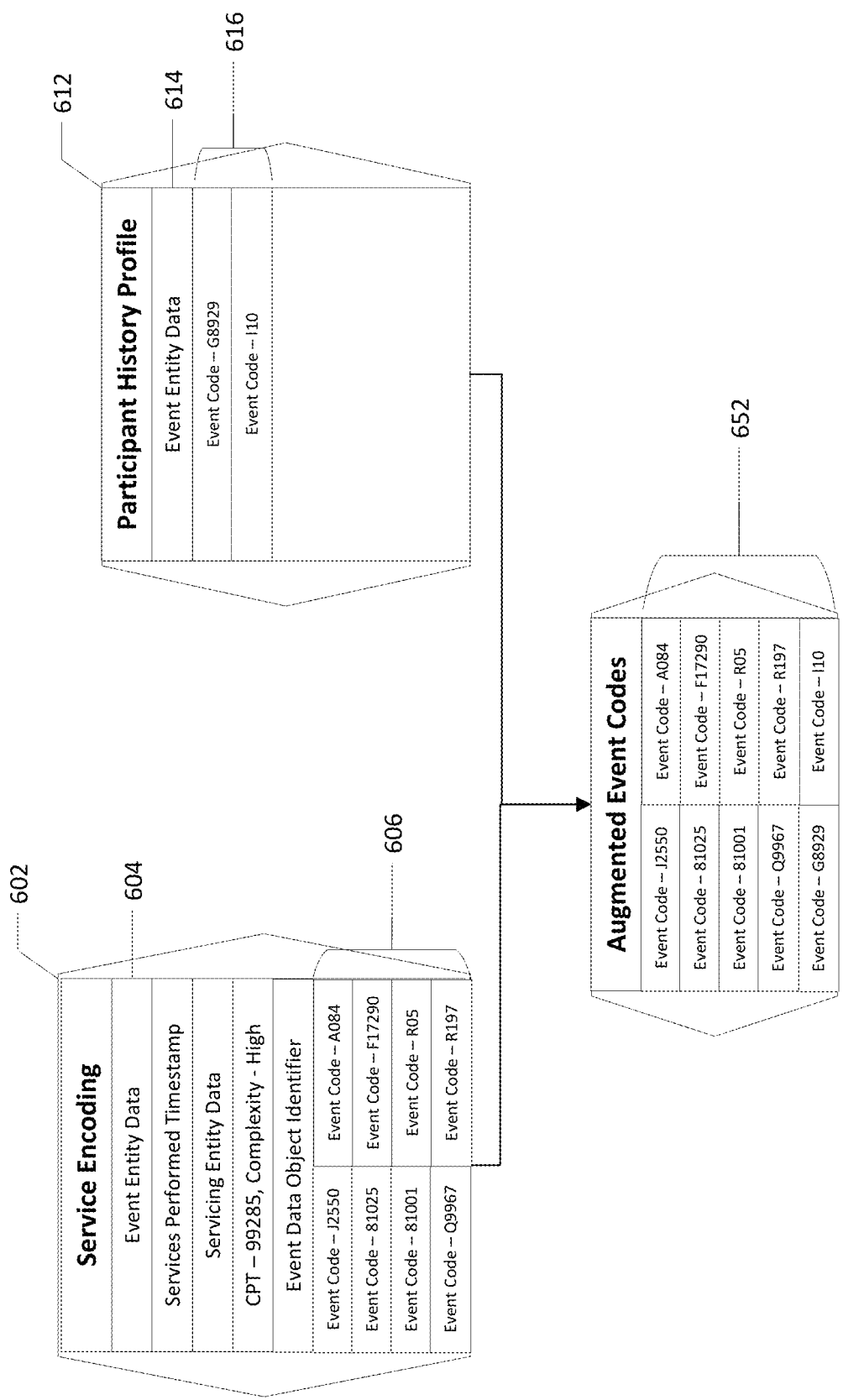
Figure 7:
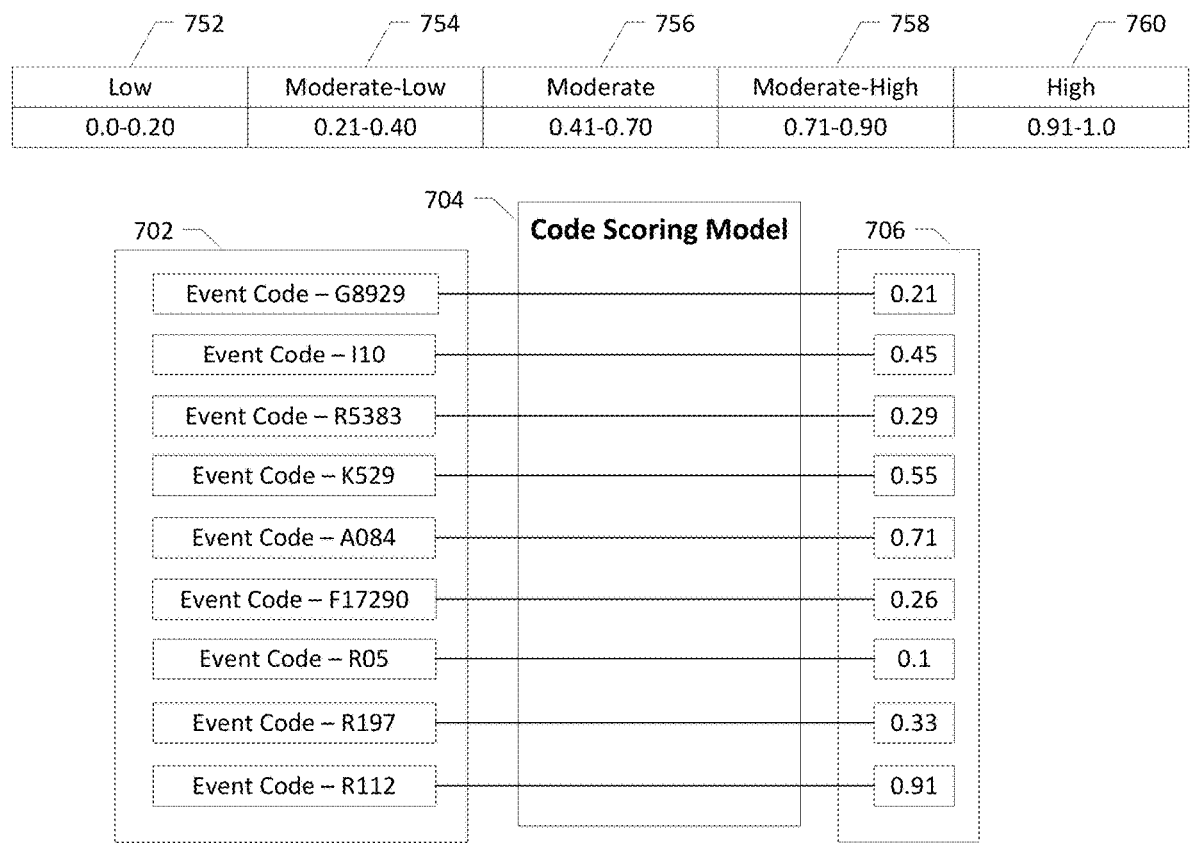
Figure 8:
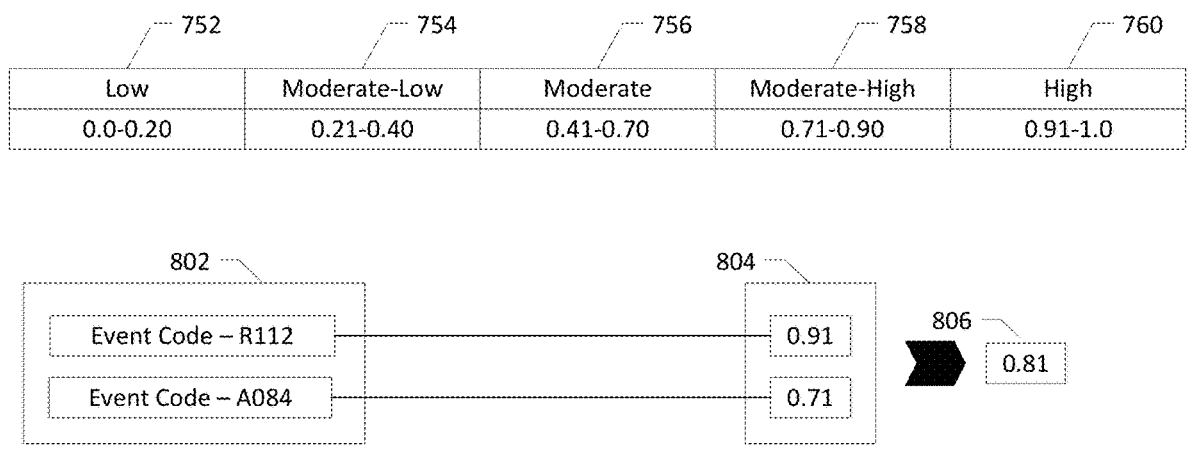
Figure 9:
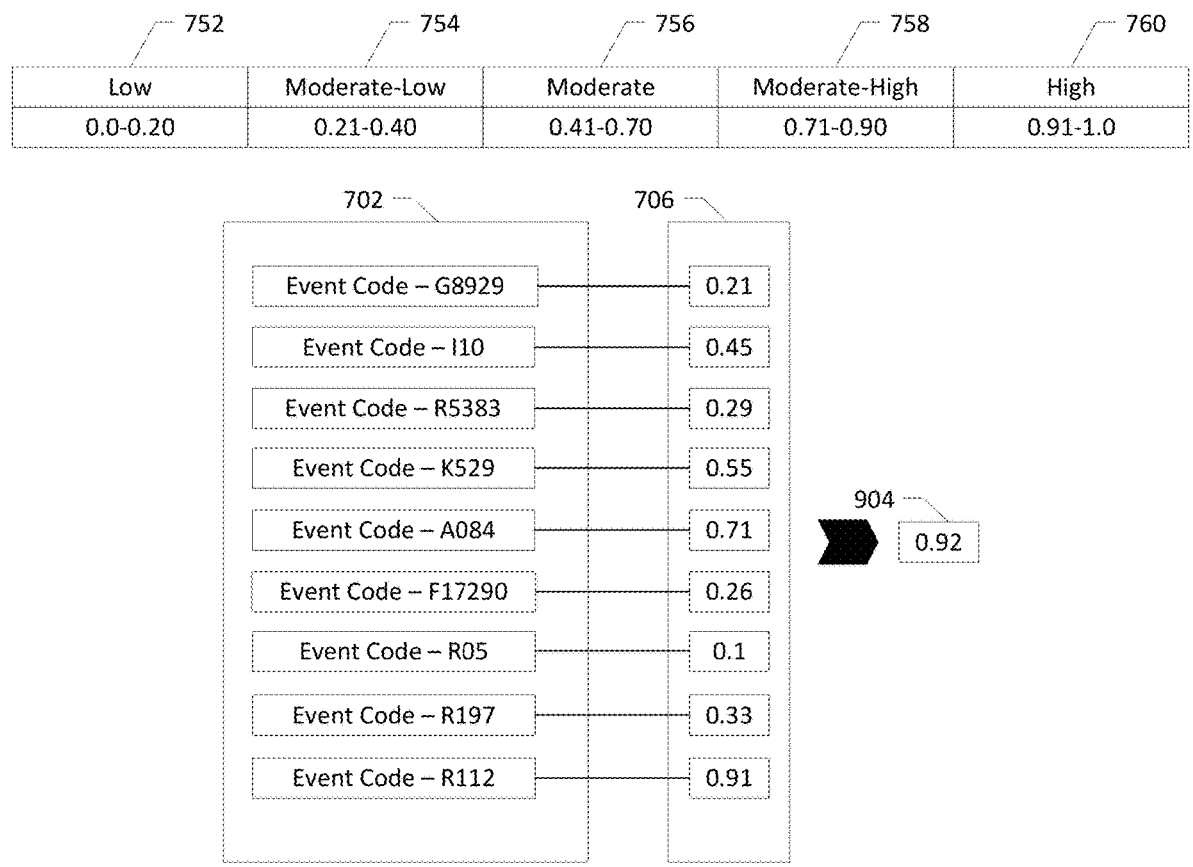
Figure 10:
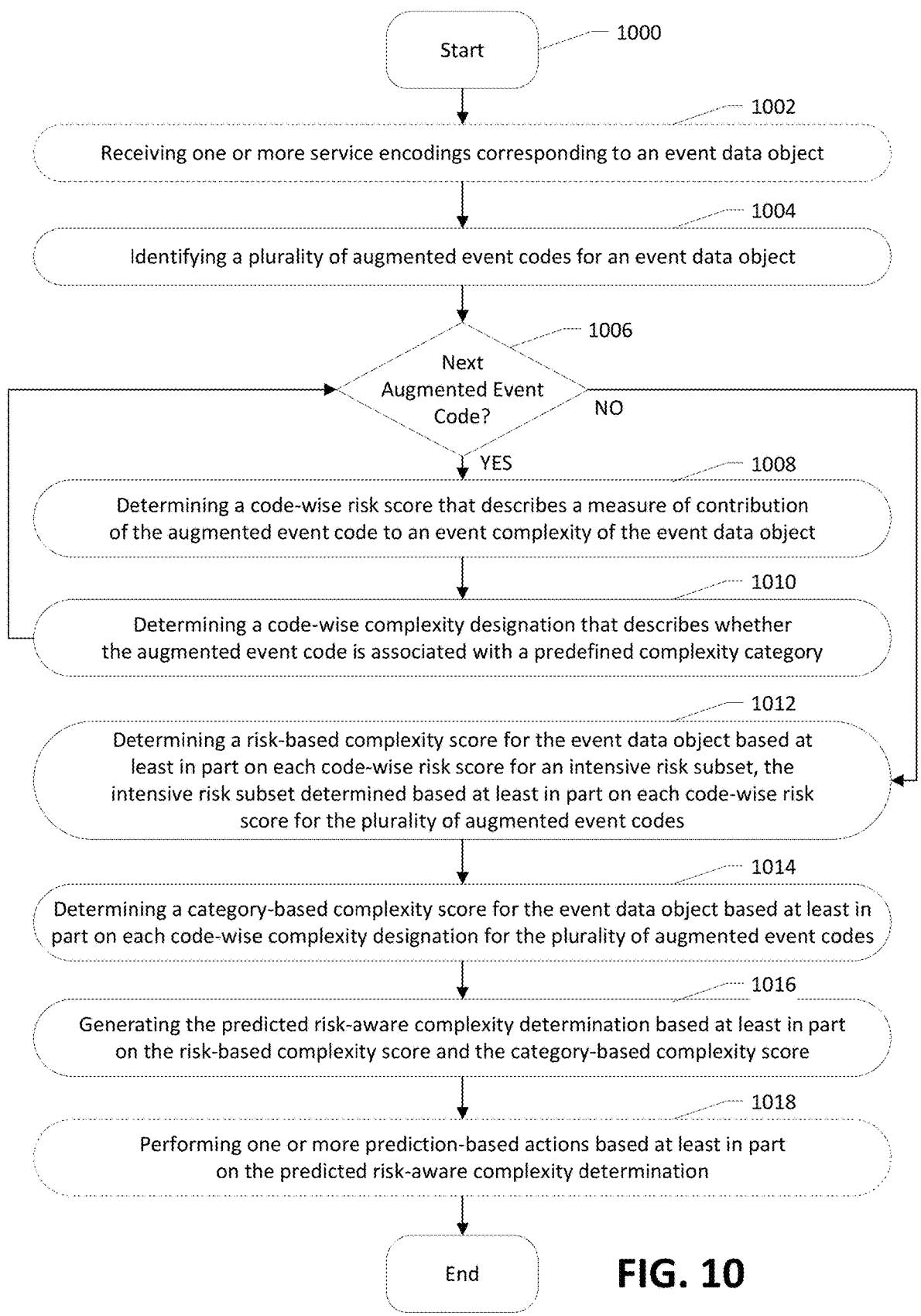
Figure 11:
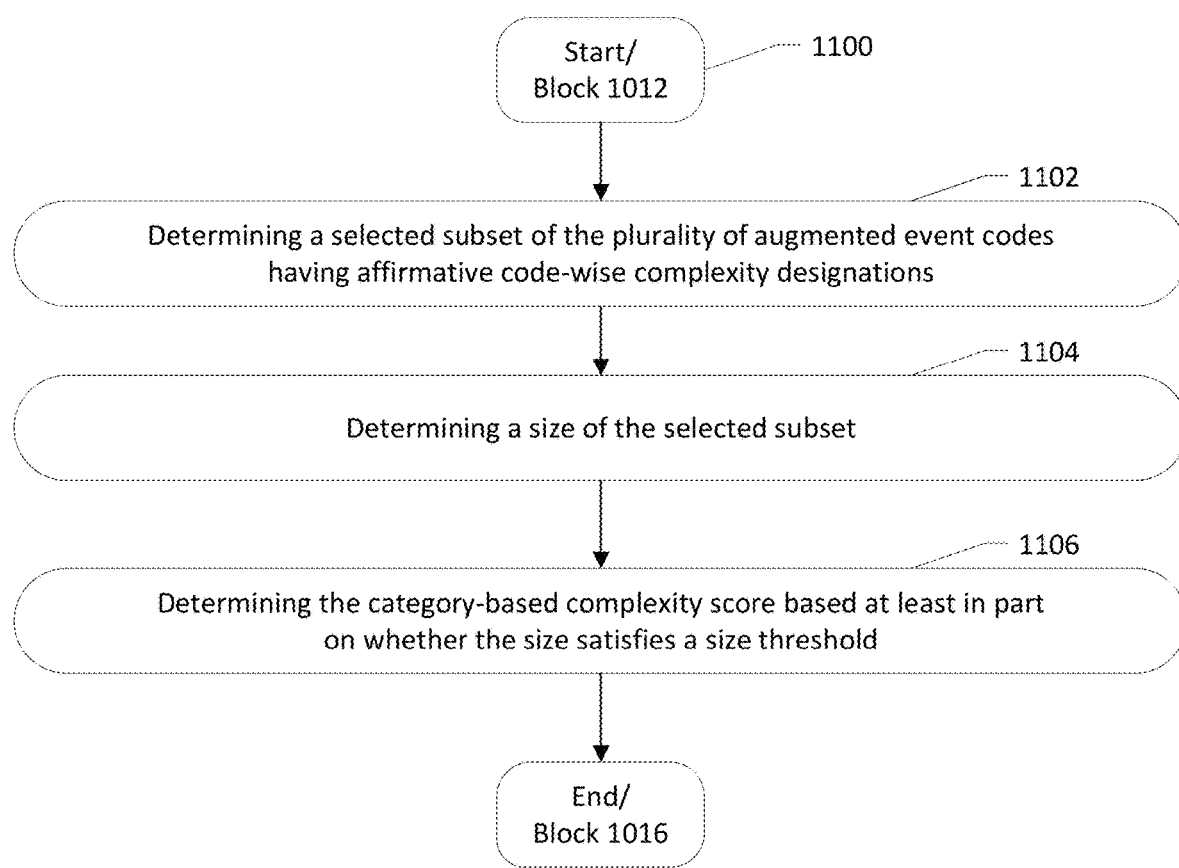
Figure 12:
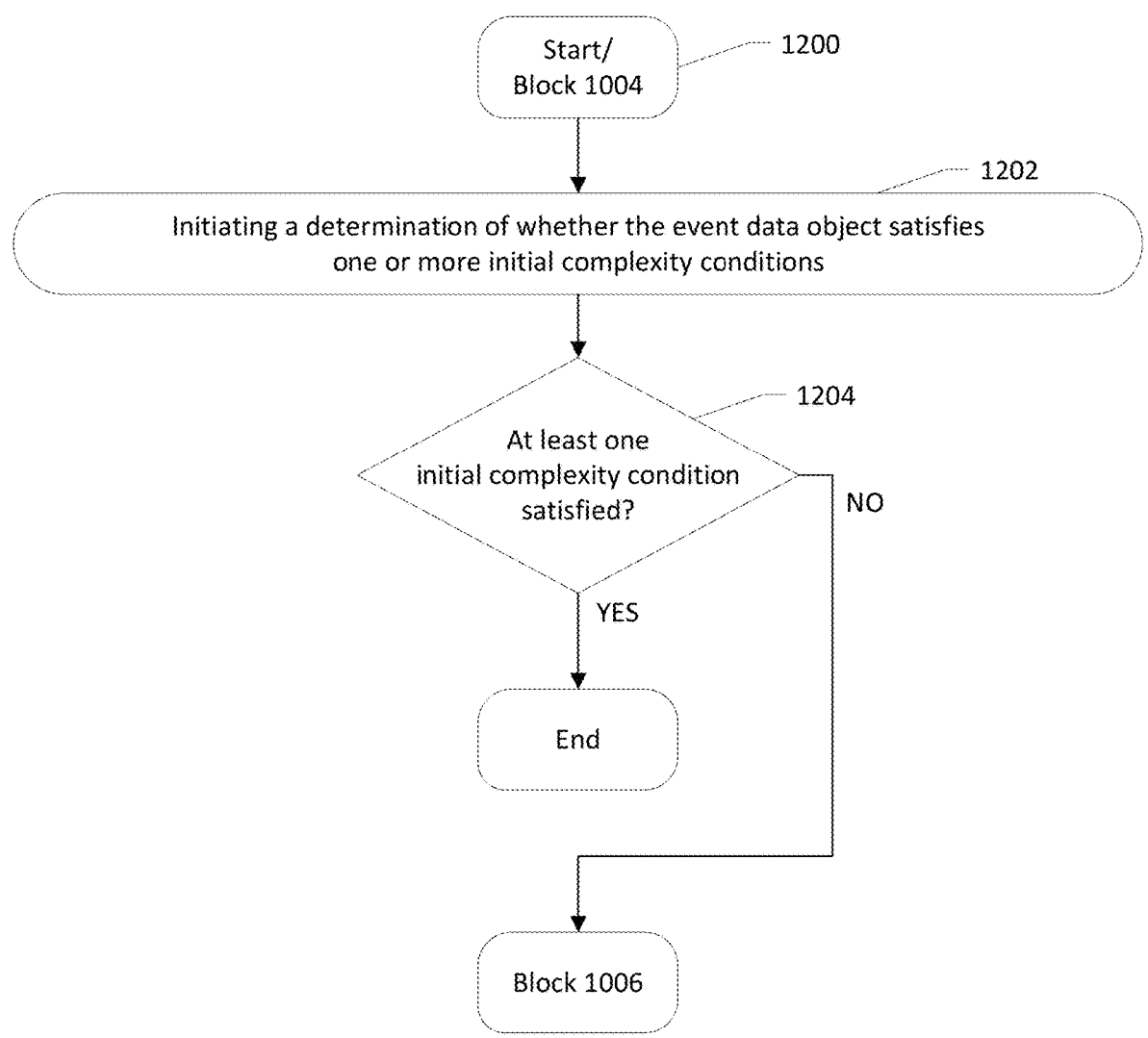
Figure 13:
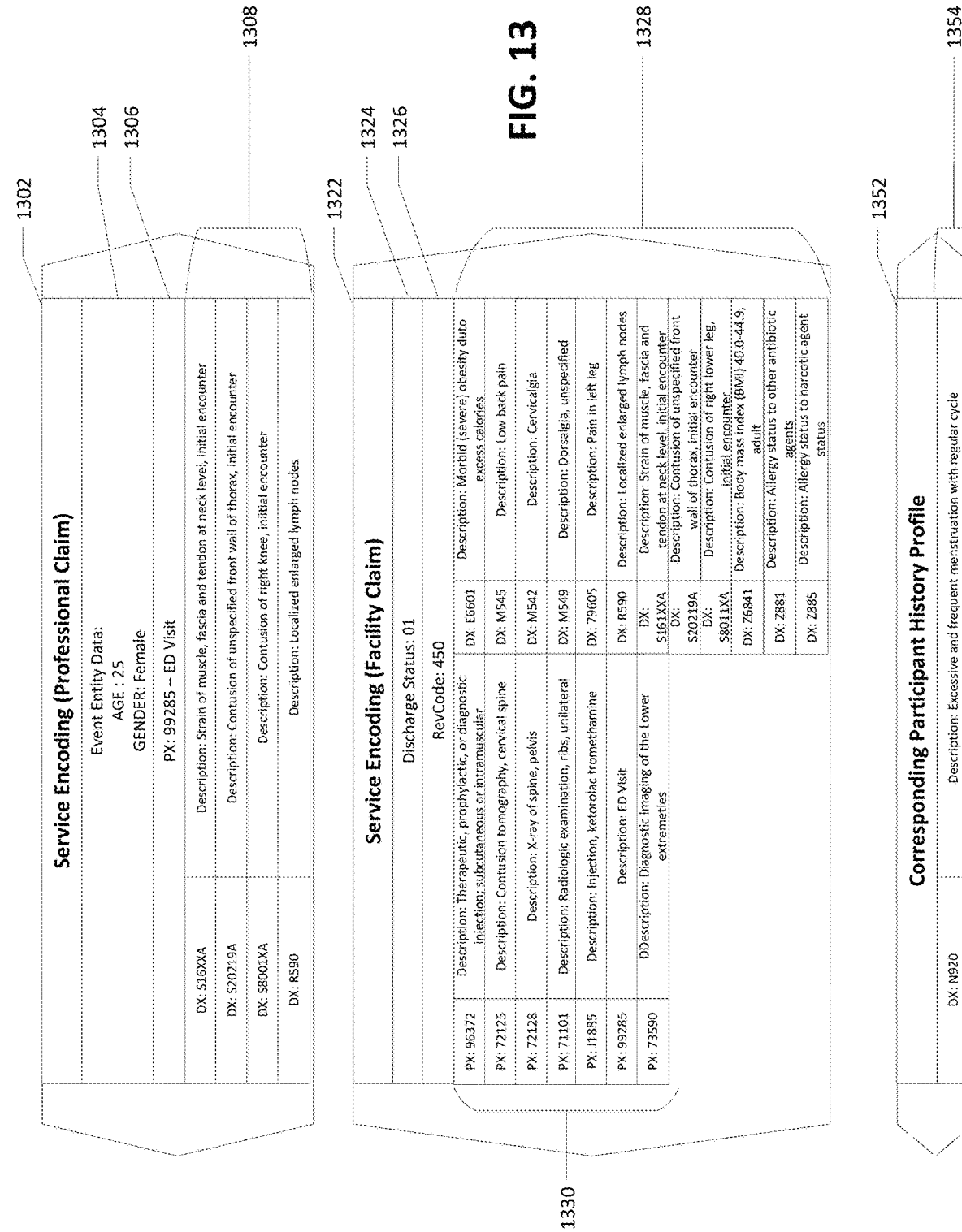
Figure 14:
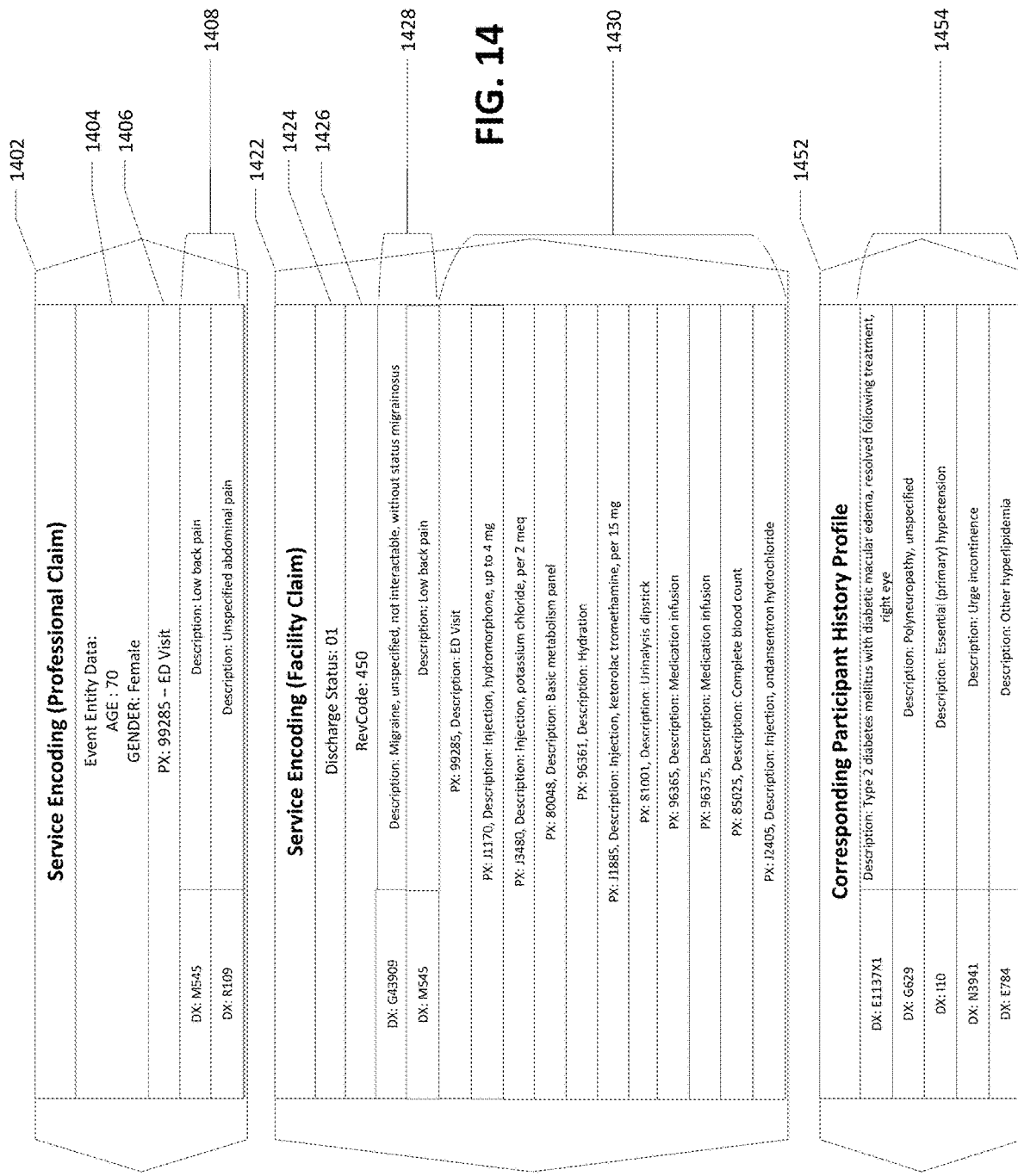

Having thus described the embodiments of the disclosure in general terms, reference now will be made to the accompanying drawings, which are not necessarily drawn to scale, and wherein:

FIG. 1 illustrates a block diagram of a system that may be specially configured within which embodiments of the present disclosure may operate;

FIG. 2 illustrates a block diagram of an example apparatus that may be specially configured in accordance with at least some example embodiment of the present disclosure;

FIG. 3 illustrates an example context in which event codes for an event data object are generated and processed in accordance with at least some example embodiments of the present disclosure;

FIG. 4 illustrates example visualizations of primary and secondary service encodings in accordance with at least some example embodiments of the present disclosure;

FIG. 5 illustrates an example visualization of generation of augmented event codes from a primary service encoding and a secondary service encoding in accordance with at least some example embodiments of the present disclosure;

FIG. 6 illustrates an example visualization of generation of augmented event codes from a service encoding and a participant history profile in accordance with at least some example embodiments of the present disclosure;

FIG. 7 illustrates an example visualization of code-wise risk score and code-wise complexity designation generation in accordance with yet some example embodiments of the present disclosure;

FIG. 8 illustrates an example visualization of intensive risk subset generation and risk-based complexity score generation in accordance with at least some example embodiments of the present disclosure;

FIG. 9 illustrates an example visualization of category-based complexity score generation in accordance with at least some example embodiments of the present disclosure;

FIG. 10 illustrates a flowchart including example operations of an example process for performing a predicted risk-aware complexity determination for an event data object utilizing a plurality of augmented event codes in accordance with at least some example embodiments of the present disclosure;

FIG. 11 illustrates a flowchart including example operations of another example process for determining a category-based complexity score in accordance with at least some example embodiments of the present disclosure;

FIG. 12 illustrates a flowchart including example operations of another example process for determining initial complexity condition satisfaction in accordance with at least some example embodiments of the present disclosure;

FIG. 13 illustrates example detailed data processed in accordance with at least some example embodiments of the present disclosure; and FIG. 14 illustrates example detailed data processed in accordance with at least some example embodiments of the present disclosure.

DETAILED DESCRIPTION

Embodiments of the present disclosure now will be described more fully hereinafter with reference to the accompanying drawings, in which some, but not all, embodiments of the disclosure are shown. Indeed, embodiments of the disclosure may be embodied in many different forms and should not be construed as limited to the embodiments set forth herein, rather, these embodiments are provided so that this disclosure will satisfy applicable legal requirements. Like numbers refer to like elements throughout.

Overview

In many contexts, a particular data system is configured to utilize data codes from various external data systems that are not verified or otherwise trustworthy to the particular data system. One example context is a complexity processing system that utilizes event codes received from one or more external systems in performing any number of determinations. The event codes may be received associated with any number of incoming transmissions from different data systems associated with different entities (e.g., service encodings associated with different entities), some of which may be verified and/or otherwise trustworthy and some of which may be unverified and/or untrustworthy. Often, such data systems cannot verify or otherwise determine whether to trust some or all of the received event codes, and thus conventionally will just process the event codes anyway.

By processing the unverified or otherwise untrustworthy event codes and performing a determination based at least in part on such unverified or untrustworthy event codes, the data system may produce resulting data via such determinations that is inaccurate. In circumstances where the data system initiates and/or performs one or more additional process(es) based at least in part on the results of such determinations, the inaccurate resulting data may further cause the data system to wrongly initiate a process and/or initiate the wrong process. In this regard, the accuracy of the resulting data produced by the data system suffers from processing the unverified and/or untrustworthy event codes. Furthermore, resources (including, without limitation: networking resources, processing resources, memory resources, and/or valuable resources) may be entirely wasted by wrongly initiating one or more process(es) based at least in part on inaccurate resulting data from such a determination. In some contexts, one or more process(es) initiated based at least in part on inaccurate data resulting from such determination(s) that utilized unverified and/or untrustworthy data may entirely degrade the data system by taking up all resources of the data system, triggering an irreversible action, and/or the like.

In attempts to avoid such downsides, a conventional data system may cause the event codes to undergo a time-consuming, arduous, expensive, and/or subjective manual review of one or more sources of the incoming event codes (e.g., a medical chart for a medical encounter) before processing occurs. Such manual review, however, may be entirely impossible in circumstances where the number of incoming event codes is too large to accommodate a manual review. Even in contexts where the number of incoming event codes is processable via human review, such a manual review can waste a myriad of other resources (e.g., human capital resources, time, capital, and the like) and/or often causes significant delay for the data system to process such event codes. Additionally, such manual review may remain inaccurate due to human subjectivity, thus leading to instances where the manual review still produces inaccurate determinations of accuracy and/or trustworthiness of one or more event codes and eliminating the purpose for such a review. Additionally, such accuracy is further affected by the inconsistency of human subjectivity, such that two identical sets of data may be processed in two different instances and result in different and/or opposing determinations. In this regard, all conventional attempts to handle unverified and/or otherwise untrustworthy data codes (such as event codes) suffer from technical deficiencies with respect to performing accurate data processing.

Embodiments of the present disclosure enable data systems to accurately perform determinations regardless of the accuracy and/or trustworthiness of incoming data codes. Embodiments of the present disclosure enable accurate determinations utilizing augmented data codes that are more accurate and/or more trustworthy than the other data codes to be processed. The augmented data codes may be generated and/or otherwise identified from a combination of sources verified or otherwise determined to be accurate and/or trustworthy and sources that may be inaccurate and/or untrustworthy. In this regard, the augmented data codes may be processed in a manner that yields accurate and/or trustworthy data regardless of the accuracy and/or trustworthiness of the individual sources of data codes. Thus, the determinations resulting therefrom may similarly be deemed accurate and/or trustworthy without requiring the nature of the source data codes be changed themselves (e.g., without requiring such data codes be accurate and/or otherwise trustworthy from the beginning).

In this regard, embodiments of the present disclosure provide various technical improvements in various technical fields. For example, by utilizing augmented data codes (e.g., augmented event codes) and processing such augmented data codes in a particular manner, embodiments of the present disclosure increase the accuracy and/or trustworthiness of data representing the results of a particular determination. Additionally or alternatively, by ensuring process(es), action(s), and/or other subsequent step(s) are initiated based at least in part on accurate determination(s), embodiments of the present disclosure reduce wasted computer resources and reduce the likelihood of errors resulting from improperly initiated action(s), process(es), and/or subsequent step(s). Additionally or alternatively still, by utilizing augmented data codes and eliminating time-consuming, arduous, costly, and/or otherwise inefficient manual review, embodiments of the present disclosure enable processing of data codes (e.g., for performing determinations associated with such data codes) in a manner that utilizes less resources and time, and thus improves overall efficiency and throughput in the operation of such embodiments.

In the context of event codes, a data system may accurately perform a predicted risk-aware complexity determination for an event data object regardless of the accuracy and/or trustworthiness of particular event code(s) corresponding to the event data object that impact or otherwise contribute to the determination. For example, the predicted risk-aware complexity determination may predict and/or otherwise assign a particular event complexity corresponding to the event data object. This predicted event complexity may be generated from all of the augmented event codes corresponding to the event data object, and/or a particular subset thereof (e.g., those that most contribute to a high complexity). By utilizing the augmented event data objects associated with a particular event data object, the event complexity determined for the event data object may be trusted as more accurate based at least in part on the wealth of available data associated with the event data object and/or event entity associated therewith. The predicted risk-aware complexity determination may subsequently be utilized for more accurately performing any of a number of prediction-based actions.

In some embodiments, by augmenting event codes for an event data object before performing predictive data analysis operations on the event codes, a proposed solution increases the likelihood that predictive data analysis operations performed on event data objects are performed on complete and accurate event codes for the noted event data objects, thus decreasing the need for performing predictive data analysis operations on event data objects again after failed initial attempts to perform predictive data analysis operations on event data objects. By augmenting service encoding(s), model(s), process(es), and/or algorithm(s) for determining and/or processing event complexity are further improved to perform more accurately. This in turn decreases the operational load on predictive data analysis frameworks that are configured to perform predictive data analysis operations on event data objects and increases the computational efficiency as well as the operational reliability of the noted predictive data analysis frameworks. In this way, various embodiments of the present invention make important technical contributions to the fields of predictive data analysis and event processing.

Definitions

In some embodiments, some of the operations above may be modified or further amplified. Furthermore, in some embodiments, additional optional operations may be included. Modifications, amplifications, or additions to the operations above may be performed in any order and in any combination.

Many modifications and other embodiments of the disclosure set forth herein will come to mind to one skilled in the art to which this disclosure pertains having the benefit of the teachings presented in the foregoing description and the associated drawings. Therefore, it is to be understood that the embodiments are not to be limited to the specific embodiments disclosed and that modifications and other embodiments are intended to be included within the scope of the appended claims. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

The term "event entity" may refer to electronically managed data representing a particular person, group, or other entity that experienced one or more real-world event(s), action(s), and/or procedure(s). In a non-limiting example context, an event entity represents a member of a group that underwent one or more action(s), procedure(s), and/or other event(s) associated with the application of medical care to the member of the group.

The term "servicing entity" may refer to electronically managed data representing a particular person, group, or other entity that performed one or more real-world event(s), action(s), and/or procedure(s) underwent by an event entity. In a non-limiting example context, a servicing entity represents a physician, a facility, a medical provider, or another medical entity that provides medical care to a patient represented by an event entity.

The term "event data object" may refer to one or more electronically managed data value(s) and/or identifier(s) that represent real-world event(s), action(s), and/or procedure(s) underwent by a particular event entity. In a non-limiting example context, an event data object may refer to electronically managed data that represents a medical encounter in a hospital environment, office environment, virtual environment, or home environment during which any number of activities associated with administration of medical assistance were performed by one or more actor(s).

The term "event complexity" may refer to electronically managed data representing a predicted complexity level associated with an event data object, where the predicted complexity level may describe whether the event data object is likely to present complicating consequences based at least in part on event codes associated with the event data object. A non-limiting example context includes an event complexity corresponding to a particular medical encounter in which a patient received particular services by one or more servicing entities. An event data object may be associated with an "submitted event complexity" submitted and/or identified by a servicing entity as associated with a particular event data object. An event data object may be associated with an "assigned event complexity" representing an event complexity determined based at least in part on a risk-based complexity score, a category-based complexity score, and/or a combination thereof, associated with a particular event data object.

The term "event code" may refer to an electronically managed data identifier that uniquely represents particular action(s), event(s), and/or procedure(s) performed associated with an event data object. In a non-limiting example context, each event code represents a diagnosis code (e.g., an International Classification of Diseases (ICD) code, a Current Procedural Terminology (CPT) code, another claim code, another procedure code, another diagnosis code, and/or the like) for medical procedure(s) performed on a particular patient during a particular medical encounter.

The term "service encoding" may refer to electronically managed data representing a set of event codes for action(s), procedure(s), and/or other event(s) underwent by a particular event entity and performed by a particular servicing entity. A service encoding is inputted and/or submitted associated with a particular servicing entity and includes an event code set corresponding to a particular event data object. In a non-limiting example context, a service encoding represents a claim submitted by a servicing entity where the claim includes event code(s) indicated for services performed by the servicing entity. Different service entities may each be associated with different service encodings. In a non-limiting example context, a service entity representing a facility (e.g., an emergency medical services delivery facility) submits a "facility service encoding" comprising event codes indicated by the facility for services performed by the facility for a particular event data object, and a physician submits a "professional service encoding" comprising event codes indicated by the physician for services performed by the physician for the particular event data object.

The term "plurality of augmented event codes" may refer to a set of event codes corresponding to an event data object that include all of the event codes associated with the service encoding(s) corresponding to the event data object. The term "augmented event code" may refer to a single event code of the plurality of augmented event codes, which may be represented in one or more of the source service encoding(s) from which the plurality of augmented event code(s) are identified. In some embodiments, the plurality of augmented event codes for an event data object comprise one or more primary event codes associated with a primary service encoding (e.g., a facility service encoding) for the event data object.

The term "code-wise complexity designation" may refer to electronically managed data representing a particular categorization of complexity of an event code, or a combination of multiple event codes based on a determined relationship, from a set of possible categorizations of complexity for event codes. Each code-wise complexity designation may be associated with a different severity and/or level of complexity across a particular range or spectrum. In a non-limiting example context, a code-wise complexity designation represents, for a particular an event code, a categorization representing the complexity of medical decision making associated with the event code. For example, the code-wise complexity designation for an event data object may describe whether the event code is associated with a moderate categorization of complexity or a categorization of complexity that is higher than the moderate categorization of complexity. In some embodiments, the set of possible categorizations embodying code-wise complexity designations are defined by an industry standard defining a particular context of medical decision making complexity.

The term "predefined complexity category" may refer to a complexity categorization from a set of possible complexity categorizations. In a non-limiting example context, a set of possible complexity categorizations corresponds to possible categorizations of a level of medical decision making performed during a medical encounter, such as a minimal complexity, a low complexity, a moderate complexity, and/or a high complexity. In some embodiments, the predefined complexity categories include a moderate categorization of complexity and any categorization of complexity that is higher than the moderate categorization of complexity. In one example context, a predefined complexity category is selected from a set of possible complexity categorizations defined in a medical decision making industry guide.

The term "code-wise risk score" may refer to a data-driven score corresponding to a particular event code, where the score indicates a contribution of the particular event code towards a higher level of complexity of an event data object that is associated with the event code. In a non-limiting example context, a code-wise risk score closer to 0 represents an event code deemed not complex (e.g., closer to the lowest possible complexity of 0), whereas a code-wise risk score closer to 1 represents an event code deemed highly complex (e.g., closer to the highest possible complexity of 1).

The term "initial complexity conditions" may refer to one or more data-driven determinations for a particular event data object that, if satisfied, indicates the event data object is associated with a particular event complexity. In an example context of medical complexity analysis, non-limiting examples of initial complexity conditions include particular predefined event codes representing particular medical scenarios and/or procedures (e.g., cardiovascular contrast studies, drug therapy with intensive monitoring, and endoscopy with risk factors), and/or representing particular behavioral health factors (e.g., suicidal ideation, major depressive disorder, and sexual abuse).

The term "intensive risk subset" may refer to electronically managed data representing the event codes of a plurality of augmented event codes corresponding to a particular event data object that are associated with a certain number of highest code-wise risk scores. In a non-limiting example context, an intensive risk subset includes two (2) augmented event codes that are associated with the highest ranked code-wise risk scores of all code-wise risk scores for the plurality of augmented event codes.

The term "risk-based complexity score" may refer to a data-driven score for an event data object that is determined based at least in part on a combination of the code-wise risk scores for each event code in an intensive risk subset. In a non-limiting example context, the risk-based complexity score represents the complexity of medical decision making on a predefined scale based at least in part on the code-wise risk scores corresponding to each event code in an intensive risk subset that includes the highest complexity event codes corresponding to a particular event data object.

The term "category-based complexity score" may refer to a data-driven score for an event data object that is determined based at least in part on whether the intensive risk subset for the event data object is associated with a required number of (e.g., three, four, and/or the like) event codes. In a non-limiting example context, the category-based complexity score represents the complexity of medical decision making on a predefined scale based at least in part on the code-wise risk scores for each of the plurality of augmented event codes corresponding to a particular event data object, which may be originally sourced from any number of service encodings.

The term "predicted risk-aware complexity determination" may refer to a data-driven determination of whether a mapping of a predicted, assigned event complexity for an event data object matches a mapping of a submitted event complexity for that event data object. The assigned event complexity is based at least in part on a category-based complexity score, a risk-based complexity score, or a combination thereof, and maps to a representation of a first predefined complexity category determined for the event data object (e.g., the event data object may be determined as associated with an assigned event complexity mapped to a moderate-high complexity category). The submitted event complexity maps to a representation of a second predefined complexity category submitted associated with the event data object (e.g., the event data object may be submitted associated with a high complexity category). In a non-limiting example context, the predicted risk-aware complexity determination compares an assigned event complexity and a submitted event complexity to determine whether the two event complexities match or do not match.

The term "primary service encoding" may refer to electronically managed data representing an event code set associated with or received from an entity trusted to provide a comprehensive set of event codes corresponding to a particular event data object. In a non-limiting example context, a primary service encoding represents a facility claim associated with a medical encounter, where the facility claim is predetermined or otherwise deemed likely more comprehensive than one or more other claim(s) (e.g., a professional claim) that may be associated with the same medical encounter.

The term "primary event codes" may refer to a set of event codes represented in a primary service encoding corresponding to a particular event data object.

The term "historical event codes" may refer to electronically managed data representing, for a particular event entity corresponding to a particular event data object, (1) an event code set corresponding to one or more historical event data objects associated with the particular event entity, and/or (2) an event code set corresponding to one or more historical event data object(s) associated with a second event entity where (A) the event code set corresponding to the one or more historical event data object(s) is determined to represent similar subject matter to the particular event data object and/or (B) the particular event entity is determined as similar to the second event entity based at least in part on one or more shared characteristics.

The term "participant history profile" may refer to electronically managed data representing a collection of data corresponding to any number of event data object(s) associated with a particular event entity and/or other event entities determined to be similar to the particular event entity based at least in part on one or more shared characteristics. A participant history profile may include any number of historical event code(s) associated with any number of event data object(s). In some embodiments, a participant history profile comprises a single data object that represents the collection of data. In other embodiments, the participant history profile comprises a plurality of data objects that are linked together to represent the collection of data. An example of a participant history profile is a data construct that includes at least a portion of a medical history of a corresponding patient event entity.

Example Systems and Apparatuses of the Disclosure

FIG. 1 illustrates a block diagram of a system that may be specially configured within which embodiments of the present disclosure may operate. Specifically, FIG. 1 depicts an example system 100 configured to enable accurate data code processing utilizing augmented data codes. The system 100 includes a complexity processing system 102, an encoding submission system 104, an additional encoding submission system 106, an entity data storage system 108, and a client device 110. One or more of such devices, for example the complexity processing system 102, the encoding submission system 104, the additional encoding submission system 106, an entity data storage system 108, and/or the client device 110, are communicable with one another and/or other computing device(s) over a communications network 112. The computing device(s), alone or in communication with one another, may provide functionality for accurate data code processing utilizing augmented data codes. It will be appreciated that the particular system depicted is illustrative of a particular example, and in other embodiments a system may include one or more other component(s), system(s), device(s), architecture(s), and/or the like. For example, the system may embody a client-server architecture, a native client-side application executing on a user-facing end terminal, a web application, and/or the like. In this regard, the particular depicted system is not to limit the scope and spirit of the present disclosure.

The encoding submission system 104 includes one or more computing device(s) embodied in hardware, software, firmware, and/or a combination thereof, that provides service encoding generation and/or submission functionality. In some embodiments, service encoding generation and/or submission functionality includes functionality for inputting any number of event code(s) associated with an event data object. The service encoding generation and/or submission functionality further includes functionality for submitting the inputted event code(s) together with information identifying the event data object associated with such event code(s). In some embodiments, the encoding submission system 104 receives input (e.g., data-driven system input automatically generated in response to particular data signals or received from another system) of the event code(s), generates a service encoding comprising the event code(s), and transmits the service encoding to one or more system(s), such as the complexity processing system 102.

The encoding submission system 104 is controlled by and/or otherwise associated with a particular servicing entity. In some embodiments, the encoding submission system 104 is associated with one or more data identifier(s) that uniquely identify the servicing entity. In this regard, such data identifier(s) may be received and/or identified to determine the servicing entity associated with a particular service encoding. In some embodiments, the encoding submission system 104 includes such data identifier(s) in the service encoding before transmission of the service encoding to an external system, such as the complexity processing system 102. Alternatively or additionally, in some embodiments, the complexity processing system 102 determines the data identifier(s) corresponding to a received service encoding (e.g., based at least in part on data and/or metadata associated with the received service encoding).

One example of an encoding submission system 104 includes a healthcare claims processing system associated with a servicing entity in the healthcare space (e.g., a hospital, a surgeon, a doctor's office, and/or the like). In this regard, a user may utilize the encoding submission system 104 to input event claims corresponding to diagnosis codes for healthcare services performed by the servicing entity during a particular medical encounter in which healthcare services were provided to a particular event entity (e.g., a patient visit to an emergency department). The particular medical event may be represented by an event data object, for example comprising a particular event identifier that corresponds to this medical encounter and particular event entity. Upon inputting all event codes, the user may utilize the encoding submission system to generate and submit a service encoding including such event codes. The service encoding may embody a medical claim corresponding to the servicing entity, and may include the event codes, identifier(s) for the servicing entity and/or event entity, and any other information relevant to processing the service encoding.

The system 100 may include any number of separate encoding submission system(s). For example, as illustrated, the system 100 optionally includes an additional encoding submission system 106. It should be appreciated that the system 100 may include any number of additional encoding submission system(s). Such separate encoding submission system(s) may be entirely distinct, associated with one another (e.g., based at least in part on associated servicing entities), and/or paired. In this regard, the complexity processing system 102 may be communicable with various separate encoding submission system(s), each of which may submit any number of service encodings associated with various event data object(s). In some embodiments, the complexity processing system 102 receives the service encodings indirectly from one or more encoding submission system(s). For example, one or more intermediary systems may receive the service encoding transmitted by the one or more encoding submission system(s), and may forward the service encoding(s) to the complexity processing system 102. In some embodiments, the complexity processing system 102 embodies a subsystem of a larger computing system, wherein one or more other subsystems of the larger computing system receives the service encodings from the separate encoding submission system(s), processes the service encodings, and/or forwards the service encodings to the complexity processing system 102.

One or more of such separate encoding submission system(s) may be associated with different servicing entities. In one example context, a first servicing entity is associated with a first encoding submission system, which the first servicing entity utilizes to generate and/or submit service encodings associated with the first servicing entity. Similarly, a second servicing entity is associated with a second, additional encoding submission system, which the second servicing entity utilizes to generate and/or submit new service encodings associated with the second servicing entity. Alternatively or additionally, in some embodiments, a single encoding submission system enables generation and/or submission of service encodings associated with two separate servicing entities. For example, a particular servicing entity may identify themselves (e.g., via authentication credentials) to access a system account associated with the servicing entity, and subsequently utilize the encoding submission system to generate and/or submit service encoding(s) corresponding to the servicing entity.

In some contexts, one or more encoding submission system(s) may submit separate service encodings associated with the same event data object. For example, a first servicing entity may submit a first service encoding corresponding to a particular event data object via a first encoding submissions system, and a second servicing entity may submit a second service encoding corresponding to the particular event data object via a second encoding submission system. The different service encodings may include a diagnosis code set including any number of diagnosis codes, and may be independent from one another. In some embodiments, each separate service encoding includes one or more data identifiers that indicate the separate service encodings are associated with one another. Alternatively or additionally, in some embodiments, service encodings associate with the same event data object are identified based at least in part on a combination of data, metadata, and/or both metadata and data for the service encodings. For example, in some embodiments, service encodings associated with the same servicing entity and event entity that are also proximate to one another in time (e.g., within the same hour, day, or other time interval) are associated with the same event data object. For example, in one example context, a first servicing entity utilizes the encoding submission system 104 to generate and/or submit a primary service encoding associated with a particular event data object, and a second servicing entity utilizes the additional encoding submission system 106 to generate and/or submit a secondary service encoding associated with the same event data object.

The complexity processing system 102 includes one or more computing device(s) embodied in hardware, software, firmware, and/or a combination thereof, that provides complexity-based processing functionality utilizing augmented event codes, as described herein. For example, in some embodiments, the complexity-based processing functionality includes functionality for identifying a set of augmented event codes. Additionally or alternatively, in some embodiments, the complexity-based processing functionality includes functionality for identifying one or more score(s), such as a risk-based complexity score and/or a category-based complexity score, associated with a set of augmented event code(s). Additionally or alternatively still, in some embodiments, the complexity-based processing functionality includes functionality for processing the score(s) generated based at least in part on the augmented event code(s), such as for performing one or more determinations based at least in part on the score(s). Additionally or alternatively still, in some embodiments, the complexity-based processing functionality includes functionality for performing one or more action(s) directly or indirectly based at least in part on the augmented event code(s), for example prediction-based action(s) based at least in part on the results of determination(s) performed based at least in part on the score(s).

The complexity processing system 102 may include any number of sub-servers, sub-systems, and/or the like. For example, in some embodiments, the complexity processing system 102 includes one or more specially configured application servers that perform one or more process(es) described herein, and includes one or more specially configured database servers and/or repositories that store particular data utilized for such process(es). Alternatively or additionally, in some embodiments, the complexity processing system 102 includes multiple sub-systems that perform independent portions of the described complexity-based processing functionality utilizing augmented event codes. For example, a first sub-system receives one or more service encoding(s) and performs one or more action(s) based at least in part on processing of such service encoding(s), and a second sub-system may generate augmented event codes based at least in part on the service encoding(s), generate complexity score(s) for the service encoding(s), perform any number of determinations associated with the service encoding(s) (e.g., predicted risk-aware complexity determinations), and provide any of the resulting and/or intermediary data associated with such functionality to the first sub-system for further processing (e.g., for use in determining prediction-based action(s) to perform).

In some embodiments, the complexity processing system 102 receives one or more service encodings including from one or more external encoding submission systems, such as the encoding submission system 104 and/or the additional encoding submission system 106. Each service encoding may include any number of event codes, and each may be associated with a particular event data object. Alternatively or additionally, in some embodiments, receiving one or more service encoding(s) may trigger the complexity processing system 102 to perform a risk-aware complexity determination associated with the event data object corresponding to such service encoding(s). Alternatively or additionally, in some embodiments, the complexity processing system 102 receives and stores service encodings for processing at a future time (e.g., to perform a risk-aware complexity determination for an event data object corresponding to one or more of the service encoding(s)). In some embodiments, additional data is received together with or immediately before or after a service encoding. For example, in some embodiments, the complexity processing system receives a service encoding together with a patient history profile, and/or particular historical event codes thereof, together with a primary service encoding or a secondary service encoding.

In one example context, the complexity processing system 102 embodies a system or subsystem that generates data representing a complexity level corresponding to medical decision making for any number of augmented event codes. The augmented event codes may be aggregated from any number of sources, for example individually submitted service encoding(s), such as a professional claim and a facility claim submitted by one or more code(s) for a particular event (e.g., a medical encounter). The augmented event codes may further be aggregated to include one or more historical event code(s), thus adding to the contextual picture of the medical decision making relevant for the particular event entity. In this regard, the complexity processing system 102 may generate one or more scores that indicate the level of complexity for medical decision making based on particular event codes (e.g., the procedure codes, diagnosis codes, relationship between said codes, and/or the like) that represent the highest complexity of medical decision making. Additionally, the complexity processing system 102 may generate one or more scores that indicate the level of complexity for medical decision making based on the aggregate contribution of each event code relevant to medical decision making of a particular event.

The entity data storage system 108 includes one or more optional computing devices embodied in hardware, software, firmware, and/or a combination thereof, that provide historical data storage functionality associated with an event entity and/or a servicing entity. For example, in some embodiments, the entity data storage system 108 includes one or more application server(s), database server(s), and/or the like, that are accessible to the complexity processing system 102 for writing data to such computing device(s) and/or reading data from such computing device(s). In some embodiments, the entity data storage system 108 is an external system accessible to the complexity processing system 102. The external system may be controlled, owned, and/or operated by a third-party entity (e.g., a central data storage utilized by various entities that process data associated with event data object(s)). Alternatively or additionally, in some embodiments, the external system may be controlled, owned, and/or operated by the same entity that controls the complexity processing system 102 (e.g., a remote or cloud data warehouse utilized by the complexity processing system 102). Alternatively or additionally still, in some embodiments, the entity data storage system 108 is a sub-system of the complexity processing system 102.

In some embodiments, the complexity processing system 102 receives data over a secured connection. Additionally or alternatively, in some embodiments, the complexity processing system 102 is accessed over a secure connection (e.g., by the client device 110). The complexity processing system 102 may perform some or all of the functionality described herein by providing results via secure file delivery, providing access to API endpoints enabling access to particular functionality, and/or the like. In some embodiments, the complexity processing system 102 generates and/or outputs one or more user interface(s) that provide the results of complexity determination(s), processing of event code(s), and/or initiating such process(es) as described herein.

In some embodiments, for example, the entity data storage system 108 is configured to store historical data associated with one or more event entities. In one example context, the entity data storage system 108 stores data embodying a participant history profile associated with each event entity for which data has previously been received and/or processed. For example, the participant history profile associated with a particular event entity may include event code(s) identified in previously received service encoding(s) associated with the event entity. Additionally or alternatively, the participant history profile may include data associated with previously processed event data objects attributed to and/or otherwise associated with the particular event entity (e.g., subject matter designation(s), complexity score(s), predicted complexity determination(s), and/or the like). In this regard, the complexity processing system 102 may access the entity data storage system 108 to retrieve such stored data for processing, for example during performance of a predicted risk-aware complexity determination for an event data object. In some embodiments, the entity data storage system 108 is additionally or alternatively configured to store data associated with servicing entities, such as data identifier(s) for a servicing entity, service classification information associated with a servicing entity, and/or the like.

The client device 110 includes one or more optional computing device(s) embodied in hardware, software, firmware, and/or a combination thereof, that enables access to the functionality of complexity processing system 102. For example, in some embodiments, the client device 110 is embodied by a user device owned, operated, and/or otherwise controlled by a particular user having access to the complexity processing system 102 (e.g., a user registered and/or otherwise associated with an authenticated account or authentication credentials for accessing the complexity processing system). Non-limiting examples of a client device 110 include a specially configured smartphone, personal computer, tablet, laptop, smart watch, smart television, wearable, and/or the like. The client device 110 may be specially configured to provide access to such functionality of the complexity processing system 102 via one or more software application(s) (e.g., "apps") installed to and/or otherwise accessible via the client device 110. In some embodiments, for example, the client device 110 provides such access via a native application associated with the complexity processing system 102 that is installed to the client device 110. Alternatively or additionally, in some embodiments, the client device 110 provides such access via a web-application accessed on a browser application installed to the client device 110. In some embodiments, the client device 110 includes one or more connected devices that provide processing, communication, networking, display, and/or other functionality.

It should be appreciated that, in other embodiments, the complexity processing system 102 is accessible directly (e.g., without utilizing a separate client device). For example, it should be appreciated that the complexity processing system 102 may include any number of computing devices, such as peripherals, displays, and/or the like, that enable a user to provide input and/or receive output. In some such embodiments, the client device 110 may be optional. Alternatively or additionally, in some embodiments the client device 110 embodies the complexity processing system 102 as an executed software application, virtual environment, and/or the like. For example, the functionality provided by the complexity processing system 102 may be installed, and in some embodiments protected by a license key or API, that enables the client device 110 to perform the functionality of the complexity processing system 102.

FIG. 2 illustrates a block diagram of an example complexity processing apparatus that may be specially configured in accordance with at least some example embodiment of the present disclosure. In some embodiments, the complexity processing system 102 is embodied by one or more computing systems, such as the complexity processing apparatus 200 as depicted and described in FIG. 2. The complexity processing apparatus 200 includes processor 202, memory 204, input/output circuitry 206, communications circuitry 208, code augmentation circuitry 210, and scores processing circuitry 212. The complexity processing apparatus 200 may be configured, using one or more of the sets of circuitry 202, 204, 206, 208, 210, and/or 212, to execute the operations described herein.

Although components and circuitry are described with respect to functional limitations, it should be understood that the particular implementations necessarily include the user of particular computing hardware. It should also be understood that certain of the components and circuitry described herein may include similar or common hardware. For example, two sets of circuitry may both leverage use of the same processor(s), network interface(s), storage medium(s), and/or the like, to perform their associated functions, such that duplicate hardware is not required for each set of circuitry. The user of the term "circuitry" as used herein with respect to components of the apparatuses described herein should therefore be understood to include particular hardware configured to perform the functions associated with the particular circuitry as described herein.

Particularly, the term "circuitry" should be understood broadly to include hardware and, in some embodiments, software for configuring the hardware. For example, in some embodiments, "circuitry" includes processing circuitry, storage media, network interfaces, input/output devices, and/or the like. Alternatively or additionally, in some embodiments, other elements of the complexity processing apparatus 200 may provide or supplement the functionality of another particular set of circuitry. For example, the processor 202 in some embodiments provides processing functionality to any of the sets of circuitry, the memory 204 provides storage functionality to any of the sets of circuitry, the communications circuitry 208 provides network interface functionality to any of the sets of circuitry, and/or the like.

In some embodiments, the processor 202 (and/or co-processor or any other processing circuitry assisting or otherwise associated with the processor) may be in communication with the memory 204 via a bus for passing information among components of the complexity processing apparatus 200. In some embodiments, for example, the memory 204 is non-transitory and may include, for example, one or more volatile and/or non-volatile memories. In other words, for example, the memory 204 in some embodiments includes or embodies an electronic storage device (e.g., a computer readable storage medium). In some embodiments, the memory 204 is configured to store information, data, content, applications, instructions, or the like, for enabling the complexity processing apparatus 200 to carry out various functions in accordance with example embodiments of the present disclosure.

The processor 202 may be embodied in a number of different ways. For example, in some example embodiments, the processor 202 includes one or more processing devices configured to perform independently. Additionally or alternatively, in some embodiments, the processor 202 includes one or more processor(s) configured in tandem via a bus to enable independent execution of instructions, pipelining, and/or multithreading. The use of the terms "processor" and "processing circuitry" may be understood to include a single core processor, a multi-core processor, multiple processors internal to the complexity processing apparatus 200, and/or one or more remote or "cloud" processor(s) external to the complexity processing apparatus 200.

In an example embodiment, the processor 202 may be configured to execute instructions stored in the memory 204 or otherwise accessible to the processor. Alternatively or additionally, the processor 202 in some embodiments is configured to execute hard-coded functionality. As such, whether configured by hardware or software methods, or by a combination thereof, the processor 202 may represent an entity (e.g., physically embodied in circuitry) capable of performing operations according to an embodiment of the present disclosure while configured accordingly. Alternatively or additionally, as another example in some example embodiments, when the processor 202 is embodied as an executor of software instructions, the instructions may specifically configure the processor 202 to perform the algorithms embodied in the specific operations described herein when such instructions are executed.

As one particular example, the processor 202 may be configured to perform various operations associated with complexity-based processing functionality utilizing augmented event codes, for example as described with respect to operation of the complexity processing system 102 and/or as described further herein. In some embodiments, the processor 202 includes hardware, software, firmware, and/or a combination thereof, that receives any number of service encoding(s) associated with a particular event data object. Additionally or alternatively, in some embodiments, the processor 202 includes hardware, software, firmware, and/or a combination thereof, that identifies and/or generates a plurality of augmented event codes for an event data object for an event data object. Additionally or alternatively, in some embodiments, the processor 202 includes hardware, software, firmware, and/or a combination thereof, that processes any number of augmented event codes. Additionally or alternatively, in some embodiments, the processor 202 includes hardware, software, firmware, and/or a combination thereof, that determines and/or otherwise generates one or more complexity score(s) based at least in part on the augmented event codes and/or scores derived therefrom. Additionally or alternatively, in some embodiments, the processor 202 includes hardware, software, firmware, and/or a combination thereof, that performs one or more determination(s) based at least in part on the generated score(s), and/or initiates one or more prediction-based action(s) based at least in part on the determination(s).

In some embodiments, the complexity processing apparatus 200 includes input/output circuitry 206 that may, in turn, be in communication with processor 202 to provide output to the user and, in some embodiments, to receive an indication of a user input. The input/output circuitry 206 may comprise one or more user interface(s) and may include a display that may comprise the interface(s) rendered as a web user interface, an application user interface, a user device, a backend system, or the like. In some embodiments, the input/output circuitry 206 may also include a keyboard, a mouse, a joystick, a touch screen, touch areas, soft keys a microphone, a speaker, or other input/output mechanisms. The processor 202 and/or input/output circuitry 206 comprising the processor may be configured to control one or more functions of one or more user interface elements through computer program instructions (e.g., software and/or firmware) stored on a memory accessible to the processor (e.g., memory 204, and/or the like). In some embodiments, the input/output circuitry 206 includes or utilizes a user-facing application to provide input/output functionality to a client device and/or other display associated with a user.

The communications circuitry 208 may be any means such as a device or circuitry embodied in either hardware or a combination of hardware and software that is configured to receive and/or transmit data from/to a network and/or any other device, circuitry, or module in communication with the complexity processing apparatus 200. In this regard, the communications circuitry 308 may include, for example, a network interface for enabling communications with a wired or wireless communication network. For example, the communications circuitry 208 may include one or more network interface card(s), antenna(s), bus(es), switch(es), router(s), modem(s), and supporting hardware, firmware, and/or software, or any other device suitable for enabling communications via one or more communication network(s). Additionally or alternatively, the communications circuitry 208 may include circuitry for interacting with the antenna(s) and/or other hardware or software to cause transmission of signals via the antenna(s) or to handle receipt of signals received via the antenna(s). In some embodiments, the communications circuitry 208 enables transmission to and/or receipt of data from a client device in communication with the complexity processing apparatus 200.

The code augmentation circuitry 210 includes hardware, software, firmware, and/or a combination thereof, that supports various functionality associated with identifying and/or otherwise generating a set of augmented event codes that includes any number of augmented event codes for a particular event data object. For example, in some embodiments, the code augmentation circuitry 210 includes hardware, software, firmware, and/or a combination thereof, that receives one or more service encoding(s), each associated with a servicing entity. Additionally or alternatively, in some embodiments, the code augmentation circuitry 210 includes hardware, software, firmware, and/or a combination thereof, that identifies one or more service encoding(s) associated with a particular event data object. In this regard, the code augmentation circuitry 210 may retrieve a participant history profile for an event entity associated with a particular event data object. Additionally or alternatively, in some embodiments, the code augmentation circuitry 210 includes hardware, software, firmware, and/or a combination thereof, that identifies an intensive risk subset of a plurality of augmented event codes. Additionally or alternatively, in some embodiments, the code augmentation circuitry 210 includes hardware, software, firmware, and/or a combination thereof, that extracts data (e.g., historical event code(s), subject matter designation(s) for historical event data object(s), selected time interval data, and/or the like) from the participant history profile for use in identifying and/or otherwise generating a plurality of augmented event codes.

It should be appreciated that, in some embodiments, the code augmentation circuitry 210 may include a separate processor, specially configured field programmable gate array (FPGA), or a specially programmed application specific integrated circuit (ASIC). Additionally or alternatively, in some embodiments, the code augmentation circuitry 210 leverages one or more other sets of circuitry to perform some or all of the operations described above.

The scores processing circuitry 212 includes hardware, software, firmware, and/or a combination thereof, that supports various functionality associated with processing augmented event code(s) to perform any of a myriad of determination(s) and/or action(s). For example, in some embodiments, the scores processing circuitry 212 includes hardware, software, firmware, and/or a combination thereof, that processes each augmented event code to determine a code-wise risk score associated with the augmented event code and determines a code-wise complexity designation associated with the code-wise risk score based at least in part on the code-wise risk score. Additionally or alternatively, in some embodiments, the scores processing circuitry 212 includes hardware, software, firmware, and/or a combination thereof, that determines a risk-based complexity score based at least in part on a subset of the augmented event codes (e.g., an intensive risk subset). Additionally or alternatively, in some embodiments, the scores processing circuitry 212 includes hardware, software, firmware, and/or a combination thereof, that determines a category-based complexity score based at least in part on the augmented event codes. Additionally or alternatively, in some embodiments, the scores processing circuitry 212 includes hardware, software, firmware, and/or a combination thereof, that generates a predicted risk-aware complexity determination based at least in part on the determined complexity score(s). Additionally or alternatively, in some embodiments, the scores processing circuitry 212 includes hardware, software, firmware, and/or a combination thereof, that initiate and/or otherwise performs one or more action(s) prediction-based action.

It should be appreciated that, in some embodiments, the scores processing circuitry 212 may include a separate processor, specially configured field programmable gate array (FPGA), or a specially programmed application specific integrated circuit (ASIC). Additionally or alternatively, in some embodiments, the scores processing circuitry 212 leverages one or more other sets of circuitry to perform some or all of the operations described above.

Additionally or alternatively, in some embodiments, one or more of the sets of circuitry 202-212 are combinable. Alternatively or additionally, in some embodiments, one or more of the sets of circuitry perform some or all of the functionality described associated with another component. For example, in some embodiments, the code augmentation circuitry 210 and the scores processing circuitry 212 are combined into a single set of circuitry embodied in hardware, software, firmware, and/or a combination thereof. Similarly, in some embodiments, one or more of the sets of circuitry, for example code augmentation circuitry 210 and/or the scores processing circuitry 212, is combined such that the processor 202 performs one or more of the operations described above with respect to each of these modules.

Example Contextual Implementation of the Disclosure

Having described example systems and apparatuses in accordance with the present disclosure, an example context in which embodiments of the present disclosure may operate will now be described. It should be appreciated that the example contexts depicted and described are provided as examples for purposes of understanding. One of ordinary skill in the art would readily appreciate that embodiments of the disclosure apply to several other contexts, including contexts related to and unrelated to those depicted and described. In this regard, the particular example contexts depicted and described herein should not limit the scope and spirit of the disclosure, and should not limit the scope and spirit of the attached claims herein.

FIG. 3 illustrates an example context in which event codes for an event data object are generated and processed in accordance with at least some example embodiments of the present disclosure. Specifically, FIG. 3 illustrates an example context for processing event codes corresponding to an event data object representing a medical encounter. The depicted context provides a visualization of a patient that receives various medical services during a medical encounter at a particular location Specifically, the illustrated context depicts a patient 302 that receives various medical services at a medical facility 350 from multiple medical professionals, such as medical support staff member 304 (e.g., an ER nurse) and a medical professional practitioner 306 (e.g., an ER doctor).

In the depicted context, the patient 302 arrives at a medical facility 350 to receive medical services for any of a myriad of reasons. The medical support staff member 304 may interact with the patient 302 and perform any of a myriad of action(s) to begin providing such medical services to the patient 302. For example, in the context of an emergency room medical facility, the medical support staff member 304 may enter the patient 302 in a particular location for examination. Additionally or alternatively, the medical support staff member 304 may perform any number of preliminary tests (e.g., blood pressure, temperature, and/or the like) and/or may request various information from the patient 302 that is necessary or useful for providing such medical services (e.g., biographical information, symptom information, medical history information, and/or the like).

The patient 302 may then interact with any of a number of other person(s) involved in providing the medical services. For example, as depicted, the patient 302 may interact with a medical professional practitioner 306. The medical professional practitioner 306 may be a specialist, surgeon, or otherwise a medical professional having a particular area of services to provide to the patient 302. In one example context, for example, the medical professional practitioner 306 may be a cardiologist that is to diagnose and/or treat particular cardiovascular symptoms experienced by the patient 302. In this regard, the medical professional practitioner 306 may interact with the patient 302 with a different end objective, and may receive the same information and/or differing information that the medical support staff member 304. For example, in some example contexts, the medical professional practitioner 306 and the medical support staff member 304 both contribute to the same patient chart for documentation of the services performed, but ultimately generate (or have generated on their behalf, such as by the same coder or different coders for each entity) different service encodings based on such shared information. The medical professional practitioner 306 may document services (e.g., tests, procedures, and/or the like) performed, reviewed, and/or the like. A separate entity, for example a coder, may generate a service encoding comprising event codes based on such documented services, and/or may generate the service encoding including contextual information regarding the patient 302 and/or the visit of the patient 302 for receiving such services (e.g., the patient's name, age, biographical data, the time of the event, and/or the like).

Each of the medical support staff member 304 and the medical professional practitioner 306, directly or indirectly for example via a coder, may generate one or more service encoding(s) associated with the services they perform. The service encodings created by the medical support staff member 304 and the medical professional practitioner 306 may each include any number of event codes corresponding to services provided, diagnoses of the patient 302, and/or other aspects of the patient 302 determined by each of the medical support staff member 304 and the medical professional practitioner 306. As each party may perform different services, interact with the patient 302 differently, and/or elicit different information from the patient 302, it should be appreciated that the service encodings generated by each party may include different event codes. In this regard, the medical support staff member 304 and the medical professional practitioner 306 may each embody an servicing entity, and the complexity processing system 102 may store and/or receive identifying data uniquely representing each of such servicing entities and the service encoding(s) associated with such servicing entities.

In some embodiments, a primary service encoding 308A and a secondary service encoding 308B is generated based at least in part on the same information. For example, the medical support staff member 304 and the medical professional practitioner 306 may each interact with the patient 302 to perform one or more medical services, and may generate data and/or documentation (e.g., a patient chart or medical record) that indicates the services performed. Another entity, for example a coder, may generate the primary service encoding 308A based on such data and/or documentation from the perspective of a professional, for example the medical professional practitioner 306. Similarly, the other entity, for example the coder or a second coder, may generate the secondary service encoding 308B based on such data and/or documentation from the perspective of a facility, for example medical facility 350. In this regard, the primary service encoding 308A may include different event code(s) from the secondary service encoding 308B, with each set of event code(s) relevant to the corresponding perspective from which each respective service encoding was generated.

In some other embodiments, as illustrated, for example, the medical support staff member 304 generates a primary service encoding 308A, and the medical professional practitioner 306 generates a secondary service encoding 308B. The primary service encoding 308A may be generated utilizing a first encoding submission system, and the secondary service encoding 308B may be generated utilizing a second encoding submission system. Alternatively, in some embodiments, the primary service encoding 308A and secondary service encoding 308B may be generated utilizing the same encoding submission system.

Each of the primary service encoding 308A and the secondary service encoding 308B may include and/or otherwise be associated with any of a myriad of information. For example, in some contexts, the primary service encoding 308A includes an event code set including all event codes inputted by the medical support staff member 304 associated with the medical services provided to the patient 302, and the secondary service encoding 308B includes an event code set including all event codes inputted by the medical professional practitioner 306 associated with the medical services provided to the patient 302. Additionally or alternatively, in some embodiments, the primary service encoding 308A includes a servicing entity identifier that uniquely identifies the medical support staff member 304. Similarly, in some embodiments, the secondary service encoding 308B includes a servicing entity identifier that uniquely identifies the medical professional practitioner 306.

In some embodiments, a primary service encoding and a second service encoding are generated based at least in part on data and/or documentation associated with the same performed services. For example, the primary service encoding 308A may represent a facility claim and the secondary service encoding 308B may represent a professional claim. The facility claim and the professional claim may include event codes (e.g., diagnosis codes, procedure codes, and/or the like) translated by different coders from the same documented services performed by each of a professional and/or facility staff (e.g., from the same medical documentation data).

Additionally or alternatively, in some contexts, the primary service encoding 308A includes an event entity identifier that uniquely identifies an event entity representing the patient 302. In some contexts, the primary service encoding 308A and/or secondary service encoding 308B may include various other data representing aspects of the patient 302 (e.g., biographical information, medical insurance information, identifying information, and/or the like). Each of the primary service encoding 308A and the secondary service encoding 308B may include a data identifier and/or otherwise be associated with a service entity representing the party submitting the service encoding. For example, the primary service encoding 308A may include or otherwise be associated with (e.g., based at least in part on the encoding submission system utilized to submit the service encoding) one or more particular data identifier(s) that uniquely identify the medical support staff member 304, and the secondary service encoding 308B may include or otherwise be associated with one or more particular data identifier(s) that uniquely identify the medical professional practitioner 306.

In some example contexts, each of the service encodings embodies a claim for medical services. For example, in this regard, the primary service encoding may embody a facility claim for services performed associated with the patient 302 during this medical encounter from the perspective of the medical facility 350. In some embodiments, multiple groups of individuals interact with the patient 302, such that the medical support staff member 304 and/or other ER staff differ from the medical group that the medical professional practitioner 306 is a part of, such that each of the groups generate and submit individual service encodings. The secondary service encoding 308B may embody a professional claim for services performed associated with the patient 302 during this medical encounter from the perspective of a particular entity, for example the medical professional practitioner 306. In this regard, each of the service encodings may subsequently be submitted to the complexity processing system 102 for processing (e.g., analysis, determination, disbursement, and/or the like). For example, the service encodings may be submitted to the complexity processing system 102 such that the complexity processing system 102 may verify the accuracy of each service encoding (e.g., with respect to the completeness, robustness, and/or trustworthiness of the event codes within one or more received service encodings, for example at least a secondary service encoding), adjust one or more of the primary service encoding 308A and/or secondary service encoding 308B, and/or perform subsequent processing action(s) based at least in part on each of the service encoding(s) and/or determinations derived therefrom, as described herein. For example, in some contexts, a primary service encoding is trusted as more complete than a secondary service encoding, such that the primary service encoding 308A is utilized to augment the secondary service encoding 308B for processing. Additionally or alternatively, a service encoding, such as the primary service encoding and/or the secondary service encoding, may be augmented by other event codes associated with the corresponding event entity (e.g., the patient 302), such as from a patient history profile.

In some contexts, one of the service encodings is determined and/or predetermined as a primary service encoding (e.g., as including data that is more comprehensive than other service encoding(s) received associated with the same event data object). For example, the service encoding generated from the perspective of the medical facility, and/or submitted on behalf of the medical facility 350 (e.g., including a corresponding identifier that uniquely identifies the medical facility 350), may be predetermined by the complexity processing system 102 as trusted to include event codes that comprehensively describe the medical services provided to the patient 302. Thus, the service encoding may be determined as a primary service encoding. In some embodiments, the primary service encoding associated with a particular event data object is utilized by the complexity processing system 102 to process another, secondary service encoding associated with the same event data object utilizing augmented event code(s) as described herein. The service encoding generated by the medical professional practitioner 306 may not be as trusted as sufficiently robust or complete, for example due to the limited scope in which the medical professional practitioner 306 focuses on interactions with the patient 302, a classification of the medical professional practitioner 306, and/or the like. For example, as illustrated, the primary service encoding 308A may be utilized to process the secondary service encoding 308B, via augmentation as described herein. Alternatively or additionally, in some embodiments, the complexity processing system 102 may identify one or more augmented event codes separate from the primary service encoding 308A and the secondary service encoding 308B. For example, the complexity processing system 102 may identify augmented event codes from a participant history profile for the patient 302 that is retrieved via the complexity processing system 102, for example utilizing one or more data portions received via the primary service encoding 308A and/or secondary service encoding 308B.

By utilizing the primary service encoding 308A and/or secondary service encoding 308B, embodiments of the present disclosure may more accurately reach one or more determination(s) associated with processing the primary service encoding 308A and/or secondary service encoding 308B. For example, the secondary service encoding 308B may be submitted including or associated with a particular submitted event complexity, and request processing of the secondary service encoding as such (e.g., for purposes of determining whether the submitted event complexity is accurate and a corresponding remittance should be issued). The determination may be performed based at least in part on augmented event codes representing diagnosis codes, procedure codes, and/or the like from individually submitted service encodings (e.g., different claims), and/or relationships between such event codes that indicate increased complexity with respect to processing the event code(s). In this regard, diagnosis codes may be processed independently, procedure codes may be processed independently, and/or any combination thereof. Embodiments of the present disclosure advantageously enable processing of the secondary service encoding 308B to perform such determinations and subsequent processing actions with improved accuracy without requiring any additional data be submitted via the corresponding servicing entities.

Example detailed contexts are depicted and described with respect to FIGS. 13 and 14. FIG. 13, for example, illustrates example detailed data processed in accordance with at least some example embodiments of the present disclosure. In this regard, the particular data depicted in FIG. 13 may result from the actions described with respect to FIG. 3, for example, and may be processed accordingly utilizing augmented event codes as described herein. In particular, the specific data depicted and described may correspond to service encodings corresponding to medical claims for services performed on a 25 year old female in an emergency department for lower back, neck, and leg pain. For purposes of description, the example is depicted and described indicating the patient received a CT scan of the neck, x-rays, and an intramuscular injection for pain.

As illustrated, FIG. 13 depicts a plurality of service encodings for processing. Such service encodings include a first service encoding 1302 and a second service encoding 1322. The first service encoding 1302 represents a professional claim (e.g., submitted by a medical professional practitioner) and may be associated with a particular event data object. The second service encoding 1322 represents a facility claim (e.g., submitted by a medical staff member associated with a medical facility, such as a hospital for example) and may be associated with the same particular event data object. In some embodiments, the first service encoding 1302 and second service encoding 1322 include and/or otherwise are received associated with particular data and/or metadata that uniquely identifies the event data object corresponding to each of the service encodings. The particular depicted service encodings my include information consolidated from a full service encoding. In this regard, it should be appreciated that the service encoding(s) may be depicted including a subset of the information included in the full service encoding, for example for purposes of simplifying the description. It will be appreciated that in other contexts, a service encoding may include additional and/or alternative fields. Such fields may be processed for purposes of performing the event complexity-related determinations described herein, and/or otherwise routing the service encoding, categorizing the service encoding, assigning the service encoding to particular entities (e.g., an event entity, an entity responsible for processing, and/or the like), and/or otherwise affecting the processing of the service encoding.

The first service encoding 1302 embodying the professional claim includes various data associated with the event entity and services performed by a first servicing entity, for example a medical professional practitioner. As illustrated, for example, the first service encoding 1302 includes event entity data 1304. The event entity data 1304 indicates the event entity represents a 25 year old female patient that received medical services. It should be appreciated that the event entity data 1304 is depicted with limited data, and in other embodiments includes additional and/or alternative information associated with the event entity (e.g., an identifier, biographical information, insurance information, and/or the like).

Each service encoding may include any number of procedure codes and/or event codes. The first service encoding 1302 embodying the professional claim further includes such data representing the services performed. For example, as depicted, the service encoding 1302 includes procedure code data 1306 that indicates a particular procedure(s) performed during the medical encounter represented by the event data object. As illustrated, the procedure code data 1306 indicates an emergency department visit, for example at a hospital location. The procedure code data 1306 includes a particular procedure code identifier that may be associated with a particular submitted event complexity.

Additionally or alternatively, the procedure code data 1306 may be associated with various event codes for particular services performed. In some embodiments, one or more types of event codes are embodied by separate data object(s) and/or data sets within a service encoding (for example, procedure codes separate from diagnosis codes). It will be appreciated that these data object(s) in some embodiments include only an identifier (e.g., a particular code identifier) and in other embodiments include additional data (e.g., a description, text notes, and/or the like).

As depicted, for example, the service encoding 1302 includes event code set 1308. The event code set 1308 includes a plurality of primary event codes associated with the event data object, for example representing medical services and/or diagnoses during a medical encounter. Each event code is associated with a particular identifier and description, for example a first event code having identifier S16XXA indicating diagnosis of a muscle strain, facia, and tendon at neck level, initial encounter, a second event code having identifier S20219A indicating diagnosis of a contusion of unspecified front wall of thorax, initial encounter, and so on. It should be appreciated that the service encoding 1302 may include an event code set 1308 having any number of event codes therein.

The second service encoding 1322 embodying the facility claim includes various data associated with the event entity's admission within a medical facility representing a second servicing entity, for example by medical staff members of the medical facility, and services performed therein. As illustrated, the second service encoding 1322 includes a discharge status 1324 indicating whether the event entity has been discharged from the medical facility. Additionally, the second service encoding 1322 includes RevCode data 1326 indicating the location and/or type of medical services performed, for example in an emergency department as depicted. It should be appreciated that in some embodiments the RevCode data 1326 is associated with or otherwise indicates a submitted event complexity.

As depicted, the service encoding 1322 includes data representing the services performed associated with the medical facility servicing entity. For example, the service encoding 1322 includes procedure code data 1330 that indicates the various procedure(s) performed during the medical encounter represented by the event data object. As illustrated, the procedure code data 1330 embodies a set of procedure codes, for example therapeutic, prophylactic, or diagnostic injection; subcutaneous or intramuscular associated with a procedure code identifier 96372, contusion of unspecified front wall of thorax, initial encounter associated with a procedure code identifier 72125, and so on. Each procedure code may be associated with any number of event code(s), for example representing medical services and/or diagnoses during the event data object.

As depicted, for example, the service encoding 1322 includes event code set 1328. The event code set 1328 includes a plurality of secondary event codes associated with the event data object. Each event code is associated with a particular identifier and description, for example a first event code having identifier E6601 indicating diagnosis of morbid (severe) obesity due to excess calories, a second event code having identifier M545 indicating diagnosis of lower back pain, and so on. Such services and/or diagnoses may be associated with performance by a second servicing entity, for example medical staff members associated with the medical facility representing the servicing entity associated with the second service encoding 1322. It should be appreciated that the service encoding 1322 may include an event code set 1328 having any number of event codes therein.

The first service encoding 1302 and second service encoding 1322 may be processed for purposes of generating data representing a complexity of the event codes therein, for example to enable a system and/or user to determine whether to approve, adjust, or deny (or perform another action) a particular one of said service encodings (e.g., a professional claim with limited contextual information, for example embodied by the first service encoding 1302) and/or each claim. Such an action may be based at least in part on a determination regarding the complexity associated with the event data object corresponding therewith, for example representing the overall complexity of medical decision making associated with the medical services performed during the medical encounter.

To improve the accuracy of the analysis of the event codes included in the service encodings, a plurality of augmented event codes may be identified. The plurality of augmented event codes may include a combination of the event codes from each of the service encodings. For example, in this regard, the plurality of augmented event codes may include all event codes from the event code set 1308 from the first service encoding 1302 combined with all event codes from the event code set 1328. In this regard, the plurality of augmented event codes provide better context into the event complexity representing the complexity of medical decision making performed during the medical encounter represented by the event data object based at least in part on the various characteristics and/or ailments of the patient represented by the event entity.

To further improve such context, augmented event codes may further be identified from a participant history profile corresponding to the event entity associated with the service encoding 1302 and 1322. For example, as illustrated, the participant history profile 1352 may be retrieved utilizing a particular event entity identifier corresponding to the event entity associated with the service encoding 1302 and 1322. The participant history profile 1352 may include various previously received and/or stored event codes associated with the event entity that contribute to the complexity of medical decision making when interacting with the event entity. The participant history profile 1352 may be identified and/or retrieved based at least in part on particular data received in the service encoding 1302 and/or 1322, or received therewith (not depicted). In particular, as depicted, the participant history profile 1352 includes an event code set 1354 including a single historical event code having an event code identifier N920 indicating excessive and frequent menstruation with regular cycle. In this regard, the plurality of augmented event codes may be generated including a combination of all event codes from the event code set 1308, 1328, and 1354.

In some embodiments, the plurality of augmented event codes are processed to generate one or more score(s) contributing to or representing a determined event complexity. For example, the plurality of augmented event codes may be processed to generate and/or otherwise determine a risk-based complexity score, which may represent a complexity of the plurality of augmented event codes based on the significance of particular high-complexity event code(s) and/or relationships between event code(s) (e.g., where the existence of particular diagnosis codes increase the complexity of a particular procedure code), and/or a category-based complexity score, which may represent a complexity of the plurality of augmented event codes based on the significance of all the event codes in combination and/or relationships between the event codes. Additionally, the plurality of augmented event codes and/or scores generated therefrom may be processed to generate and/or otherwise determine a predicted risk-aware complexity determination that represents the overall complexity based on the individual components.

The plurality of augmented event codes may be processed in accordance with any of the methodologies described herein. For example, in some embodiments, an intensive risk subset of the plurality of augmented event codes is identified that includes the two augmented event codes indicated as associated with the highest risk represented by a code-wise risk score for each augmented event code. Such augmented event codes may be identified as the event code associated with event code identifier R590 and the second highest associated with event code identifier S161XXA. A weight may be identified for each of these augmented event codes and utilized to generate a risk-based complexity score, for example based at least in part on combination of the weighted scores for each of the augmented event codes of the intensive risk subset. For example, the R590 event code may be assigned a weight of 400 and the S161XXA event code may similarly be assigned a weight of 400. The risk-based complexity score may be generated by adding the individual weights together, for a total of 800. In some embodiments, the weight assigned to a particular event code is predetermined, from example such that a lookup table may be accessed to determine the particular weight. Alternatively or additionally, in some embodiments a determinable and/or predefined algorithm is utilized to determine the weight for a particular event code. In one example context, an industry standard algorithm is defined for determining a weight for a particular event code.

A weight of a particular event code may be determined in any of a myriad of manners. In some embodiments, a weight for a particular event code is determined based at least in part on a trusted and/or industry standard resource. The industry standard resource provides an orientation with respect to complexity in a particular context, such as medical decision making, at various levels of breadth, including example(s) of complexity for an event code and/or combination of event code(s). For example, in some embodiments, an individual event code and/or a combination of event codes based on an industry standard resource(s) may be assigned a predetermined weight based on comparison to known and/or previously provided complexity for other event code(s) and/or combinations of event codes. Such examples may indicate particular event code(s) and/or combinations that are indicative of highly complex medical decision making, such that other event code(s) may be weighted on a relative basis to such example(s). For example, a first event code may be indicated by an industry resource as associated with a high complexity, and thereby assigned a particular weight, such that other event codes determined or otherwise indicated as less complex may be assigned lower weights and/or more complex event code(s) may be assigned higher weights. Such weights may be defined by a particular expert (e.g., a subject matter expert), an algorithm, a specially trained model (e.g., a machine learning model, an artificial intelligence model), and/or the like. In this regard, the individual event codes and/or combination of event codes may be weighted relative to one another on an absolute scale. and/or relative based on their relationship(s) with other event code(s) (including combinations of event codes that together indicate a higher complexity). In one example context, first event codes in a first service encoding indicate an event entity having experienced dizziness and giddiness may be determined associated with a first complexity designation and/or weight alone. However, in a circumstances where second event codes in the first service encoding or augmented from another service encoding or participant history profile indicate medical imagery such as a CT scan or MRI performed during the same event data object, the combination of the first and second event codes may map to and/or otherwise be determined to represent higher a higher complexity.

In some embodiments, the complete plurality of augmented event codes is then evaluated to determine whether additional complexity is contributed by the number of independent event codes (even if such event codes are individually contribute little to overall complexity, for example are low and/or moderate complexity). In some embodiments, for example, the 17 distinct augmented event codes represented in the plurality of augmented event codes generated including a combination of all event codes from the event code set 1308, 1328, and 1354 contribute an additional weight represented by a category-based complexity score for the event data object. Based at least in part on a size threshold, the 12 distinct augmented event codes may be determined to contribute an additional 300 weight representing a category-based complexity score.

A predicted risk-aware complexity determination may be performed based at least in part on the individual complexity scores generated from the augmented event codes. For example, the complexity scores may be summed for a total weight, or score, of 1100. In this regard, the total weight represents the overall risk and complexity of the medical decision making represented by the event complexity corresponding to the event data object. Embodiments may map the score to a particular event complexity, for example based at least in part on predefined ranges of scores corresponding to each predetermined complexity designation. In the example depicted, the total score of 1100 may be mapped to a moderate-high complexity lower than the submitted event complexity corresponding to the procedure code of 99285. In this regard, embodiments may proceed to initiate and/or otherwise perform prediction-based action(s) accordingly, for example by assigning the predicted event complexity to each of the first service encoding 1302 and second service encoding 1322, and reducing and/or denying such service encoding due to the reduced predicted event complexity compared to the submitted event complexity accordingly.

FIG. 14 illustrates example detailed data processed in accordance with at least some example embodiments of the present disclosure. In this regard, the particular data depicted in FIG. 14 may similarly result from the actions described with respect to FIG. 3, for example, and may be processed accordingly utilizing augmented event codes as described herein. In particular, the specific data depicted and described may correspond to service encodings corresponding to medical claims for services performed on a 70 year old female with type-2 diabetes and hyperlipidemia in an emergency department for a headache and low back pain. For purposes of description, the example is depicted and described indicating the patient received medical lab work, hydration, and medical infusion.

As illustrated, FIG. 14 depicts a plurality of service encodings for processing. Such service encodings include a first service encoding 1402 and a second service encoding 1422. Akin to the service encodings described with respect to FIG. 13, the service encoding 1402 represents a professional claim and may be associated with a particular event data object. The second service encoding 1422 represents a facility claim and may similarly be associated with the same particular event data object. It should be appreciated that the data portions of the service encoding 1402 may include similar data and function similarly to the similarly named and described data portions of the service encoding 1302. For example, first service encoding 1402 includes event entity data 1404 representing a 70 year old female patient, and may be similarly structured and function akin to the event entity data 1304 as described with respect to FIG. 13. Similarly, the procedure code data 1406 and the event code set 1408 may include similar data and function similarly to the similarly named procedure code data 1306 and event code set 1308 depicted and described with respect to FIG. 13. Further, it should be appreciated that the specific procedures and diagnoses or services represented thereby may differ without deviating from the scope and spirit of this disclosure.

The second service encoding 1422 embodies a facility claim similar to the second service encoding 1322 representing a facility claim as depicted and described with respect to FIG. 13. For example, the second service encoding 1422 includes a discharge status 1424 indicating whether the event entity has been discharged from the medical facility, and a RevCode data 1326 indicating the location and/or type of medical services performed. Additionally, the second service encoding 1422 includes a procedure code set 1430 and an event code set 1428. It should be appreciated that such data may include similar data and function similarly to the similarly named procedure code data 1330 and event code set 1328 as depicted and described with respect to FIG. 13. Further, it should be appreciated that the specific procedures and diagnoses or services represented thereby may differ without deviating from the scope and spirit of this disclosure.

The participant history profile 1452 embodies a participant history profile corresponding to the particular event entity associated with the first service encoding 1402 and the second service encoding 1422 (e.g., the 70 year old female patient). The participant history profile 1452 may be utilized to identify particular augmented event codes that provide further context for purposes of determining an event complexity for the event data object associated with the first service encoding 1402 and second service encoding 1422. It should be appreciated that the participant history profile 1452 may be retrieved utilizing a particular event entity identifier corresponding to the event entity associated with the first service encoding 1402 and/or second service encoding 1422.

The various event codes indicated in the participant history profile 1452 may contribute to the complexity of medical decision making when interacting with the event entity associated with the participant history profile 1452. For example, as illustrated, the participant history profile 1452 includes an event code set 1454 including various historical event codes associated with the particular event entity. The event code set 1454 includes a first event code having an identifier E1137X1 indicating the type 2 diabetes mellitus with diabetic macular edema in the right eye that was resolved following treatment, a second event code having an identifier G629 indicating polyneuropathy, unspecified, a third event code having an identifier I10 indicating essential (primary) hypertension, and so on. Such event codes may further be utilized to augment the event codes from the service encodings in the first service encoding 1402 and second service encoding 1422 to give a clearer picture regarding the complexity of medical decision making in providing medical services to the 70 year old patient represented by the event entity. In this regard, the plurality of augmented event codes may be generated including a combination of all event codes from the event code set 1408, 1428, and 1454.

The plurality of augmented event codes may be evaluated to determine if one or more initial complexity conditions are satisfied. For example, the first service encoding only includes an event codes that alone are associated with a relatively low complexity. Embodiments of the present disclosure may maintain any of a number of initial complexity conditions indicating that the event complexity is high due to satisfaction of the initial complexity condition(s). In this regard, the augmented event codes may be processed and/or otherwise checked against the initial complexity condition(s) to determine whether such initial complexity condition(s) are satisfied. In one particular context, embodiments may maintain one or more initial complexity condition(s) that bypass the need for further event complexity predicting in circumstances where high event complexity is indicated by the presence of an event entity age above a particular age threshold and the presence of two or more chronic conditions. For example, in a circumstance where the age threshold is 65, such an initial complexity condition is met upon comparing the age associated with the event entity (e.g., 70) with said age threshold. Additionally, as depicted, the augmented event codes identified from the first service encoding 1402, second service encoding 1422, and participant history profile 1452 includes two chronic conditions (e.g., diabetes represented in an augmented event code determined from the participant history profile as the source, and hyperlipidemia represented in an augmented event code similarly determined from the participant history profile as the source).

In such contexts where the initial complexity condition(s) are determined to be satisfied, the received service encoding(s) embodying the claims may bypass additional event complexity prediction as described herein. For example, such service encoding(s) may instead be processed based at least in part on a submitted event complexity received therewith. For example, one or more prediction-based actions may be initiated and/or performed based at least in part on the submitted event complexity without generating a predicted risk-aware complexity determination, as described herein. Such processing may still be trusted as the event complexity indicated by the augmented event codes satisfied sufficient conditions indicating high complexity based at least in part on determinable conditions represented therein.

Example Data Representations of the Disclosure

Having described example systems, apparatuses, and contexts in accordance with the present disclosure, example data representations as processed in accordance with the present disclosure will now be described. It should be appreciated that the example data representations depicted and described are provided as examples for purposes of understanding. One of ordinary skill in the art would readily appreciate that embodiments of the disclosure may utilize various other configurations of data object(s) having the same properties, additional properties, less properties, and/or reduced properties, including data properties related to and unrelated to those depicted and described in the figures. In this regard, the particular example data representations depicted and described herein should not limit the scope and spirit of the disclosure, and should not limit the scope and spirit of the attached claims herein.

FIG. 4 illustrates example visualizations of primary and secondary service encodings in accordance with at least some example embodiments of the present disclosure. Specifically, FIG. 4 depicts a visualization of a primary service encoding 402 and a secondary service encoding 452. It should be appreciated that, in some embodiments, the primary service encoding 402 and/or secondary service encoding 452 include one or more additional and/or alternative data properties. For example, in some embodiments, the primary service encoding 402 and/or the secondary service encoding 452 may include a data identifier indicating whether the service encoding is a primary or secondary service encoding.

In some embodiments, a service encoding includes a form identifier, or is processable to determine a form identifier, that indicates or otherwise corresponds to a category of form embodying the service encoding. In one particular example context, for example, a service encoding includes an identifier indicating the service encoding is embodied by a file data object representing an instance of HCFA form 1500, or is processable (e.g., based on the data fields represented in the service encoding, image processing, and/or the like) to determine the service encoding represents an instance of HCFA form 1500. The HCFA form 1500 may correspond or otherwise be indicated as representing a secondary service encoding (e.g., a professional claim), for example based on a static association between this form identifier and a type of service encoding. Alternatively, a service encoding may include an identifier indicating the service encoding is embodied by a file data object representing an instance of form UB-04. The UB-04 form may correspond to or otherwise be indicated as representing a primary service encoding (e.g., a facility claim), for example based on a static association between this form identifier and a type of service encoding. It should be appreciated that the primary service encoding 402 may be received from the same system or a different system from the secondary service encoding 452. Similarly, it should be appreciated that the primary service encoding 402 and the secondary service encoding 452 may be received at the same time or at different times via such system (e.g., via an encoding submission system). In some embodiments, any of the depicted and/or described data properties may be embodied as data and/or metadata associated with the data object(s) depicted and described.

As illustrated, the primary service encoding 402 includes event entity data 404. The event entity data 404 may include any data utilized to identify the event entity associated with an event data object, and/or any other detail information associated with the event entity. Such event entity data 404 may include biographical information corresponding to the event entity, service coverage information (e.g., an insurance identifier), and/or the like. In this regard, the event entity data 404 may be utilized to identify the event entity and/or perform any number of determinations associated with the event entity.

In some embodiments, the primary service encoding 402 includes a services performed timestamp 405. The services performed timestamp may represent a date, datetime, or other indicator of when the servicing entity associated with the primary service encoding 402 is recorded to have been performed by the particular services represented by the primary service encoding 402. In one example embodiment, the services performed timestamp represents a date embodied as a combination of a month, a day, and a year.

The primary service encoding 402 additionally or alternatively includes servicing entity data 406. The servicing entity data 406 may include any data utilized to identify the servicing entity associated with an event data object, and/or any other detail information associated with the servicing entity. Such servicing entity data 406 may include a provider identifier, entity information (e.g., registered entity name, location, employer identification number, and/or the like), and/or other information associated with the servicing entity. In some embodiments, the servicing entity submits, via the primary service encoding, a particular servicing entity identifier that the complexity processing apparatus 200, for example, may utilize to perform a lookup of the corresponding servicing entity in a database maintained by and/or otherwise accessible to the complexity processing apparatus 200 upon receiving the primary service encoding 402. In some embodiments, the servicing entity data 406 comprises metadata automatically included in the primary service encoding 402 by the encoding submission system utilized to input the primary service encoding 402, for example IP address information corresponding to a particular servicing entity.

The primary service encoding 402 additionally or alternatively includes submitted event complexity data 408. In some embodiments, the submitted event complexity data 408 embodies or otherwise represents a first event code associated with the particular event (e.g., a procedure code). The submitted event complexity data may identify a particular submitted event complexity and/or be utilized to derive a particular submitted event complexity associated with an event data object. For example, in some embodiments, the submitted event complexity data 408 includes data identifier(s) that uniquely identify a particular classification of event data object based at least in part on the nature of the services performed during the event data object. In one such example context (e.g., the context of medical encounters), such data identifier(s) may include CPT codes. In some such embodiments, the complexity processing system may maintain a database and/or lookup table that maintains links such data identifier(s) with a corresponding submitted event complexity required to process the service encoding. In this regard, the complexity processing apparatus 200 may utilize the data identifier(s) therein to determine the submitted event complexity for the primary service encoding from said lookup table and/or database. Alternatively or additionally, in some embodiments, the primary service encoding comprises submitted event complexity data 408 that directly represents the submitted event complexity for the primary service encoding 402.

The primary service encoding 402 additionally or alternatively includes an event data object identifier 410. The event data object identifier 410 may include data that directly identifies the event data object associated with the primary service encoding 402, and/or that may be utilized to indirectly derive the event data object associated with the primary service encoding. For example, in some embodiments, the event data object identifier 410 includes a datetime, location, predetermined configuration of sub-identifier(s), alphanumeric data identifier(s) inputted by the servicing entity, and/or the like. It should be appreciated that the event data object identifier 410 may include one or more portions of data in any configuration and/or manner that is similarly processable by the complexity processing apparatus 200.

In some embodiments, some or all of the event data object identifier may be compared with and/or otherwise utilized to identify whether the primary service encoding 402 and an additional service encoding (e.g., the secondary service encoding 452) are associated with the same event data object. For example, in some embodiments the event data object identifier includes a datetime that indicates the duration of an event data object. In this regard, service encodings associated with event data object identifiers representing overlapping datetimes (e.g., in whole or in part) may be processed as associated with the same event data object.

The primary service encoding 402 additionally or alternatively includes an event code set 412 including any number of primary event codes. Each primary event code in the event code set 412 may be automatically inputted into the primary service encoding 402 and/or manually inputted by a user associated with the servicing entity, for example. In this regard, the event code set 412 may include data that uniquely indicates action(s), determination(s), and/or other data relevant to the event data object associated with the primary service encoding.402. For example, the event codes in the event code set 412 may embody any event code automatically or manually identified and/or submitted as contributing towards a higher level event complexity.

It should be appreciated that the event code set 412 may include any number of event codes. For example, as depicted, the event code set 412 includes eight total event codes. In other embodiments, the event code set 412 may include more or less event codes. In some embodiments, service encodings including more event codes may be determined as more holistic and/or trustworthy as complete. For example, a primary service encoding 402 may be determined as such over the secondary service encoding 452 as the secondary service encoding 452 includes significantly less event codes. In one example context, the primary service encoding 402 embodies a facility claim submitted for processing by a medical facility and the secondary service encoding 452 embodies a professional claim submitted for processing by a particular practitioner or medical group.

FIG. 4 further depicts the secondary service encoding 452. The secondary service encoding similarly includes event entity data 454, servicing entity data 456, submitted event complexity data 458, event data object identifier 460, and an event code set 462. The secondary service encoding 452 includes several similarly named data portions. It should be appreciated that the similarly named data portions between the primary service encoding 402 and the secondary service encoding 452 may serve the same purpose, but may include differing data values specific to the secondary service encoding 452. For example, the event entity data 454 may similarly identify the same event entity, and the servicing entity data 456 may identify a different servicing entity. Additionally or alternatively, the event data object identifier 460 may include the same data as the event data object identifier 410, an overlapping time interval, and/or other data that otherwise indicates that the event data object corresponding to the primary service encoding 402 and the secondary service encoding 452 are the same.

In some embodiments, the secondary service encoding 452 includes a services performed timestamp 455. The services performed timestamp may represent a date, datetime, or other indicator of when the servicing entity associated with the secondary service encoding 452 performed the particular services represented by the secondary service encoding 452. In one example embodiment, the services performed timestamp represents a date embodied as a month, day, and year. In some embodiments, the secondary service encoding includes services performed timestamp 455 that is the same as or otherwise equivalent to the services performed timestamp 405 for the primary service encoding 402. In one example context, two services performed timestamps are equivalent in a circumstance where such data represent the same date (e.g., same month, day, and year) for services performed. It will be appreciated that, in some embodiments, the services performed timestamp associated with one or more service encoding(s) may be used to correlate service encodings associated with a particular event data object, for example based at least in part on whether the services performed timestamps fall within a defined time range from one another (e.g., same day, within a 24-hour period, and/or the like).

In some embodiments, one or both of the primary service encoding 402 and/or the secondary service encoding 452 is/are utilized to determine an event complexity corresponding to the event data object identifier therein, perform one or more determination(s) associated therewith, and/or initiate one or more prediction-based actions based at least in part on the event complexity. For example, the primary service encoding 402 and the secondary service encoding 452 may be utilized to identify a plurality of augmented event codes, which may be processed to more accurately determine an event complexity corresponding to the identifiable event data object. In some embodiments, the assigned and/or otherwise predicted event complexity may be utilized to perform prediction-based action(s) associated with the service encoding(s) and/or event data object associated therewith. For example, in some embodiments, the primary service encoding 402 is utilized in conjunction with the secondary service encoding 452 to identify and process a plurality of augmented event codes, determine a predicted risk-aware complexity determination identifying an event complexity for the event data object identified by the service encodings, and performing a prediction-based action embodying approved, adjusted, or denied processing of the secondary service encoding 452 (and/or the primary service encoding 402) based at least in part on the event complexity embodied by the predicted risk-aware complexity determination.

In some embodiments, the secondary service encoding 452 is identified as secondary (or otherwise not primary) based at least in part on one or more portions of data in the secondary service encoding 452. For example, the secondary service encoding 452 may be identified as secondary based at least in part on the servicing entity identified via the servicing entity data 456. Alternatively or additionally, in some embodiments, the secondary service encoding 452 may be identified as secondary based at least in part on the decreased number of secondary event codes within the event code set 462 as compared to the event code set 412. In some embodiments, a primary service encoding and/or secondary service encoding(s) are not explicitly determined, and all service encodings are processed as described herein for purposes of performing determinations of the event complexity associated with each service encoding.

FIG. 5 illustrates an example visualization of generation of augmented event codes from a primary service encoding and a secondary service encoding in accordance with at least some example embodiments of the present disclosure. Specifically, FIG. 5 depicts an example plurality of augmented event codes 502. The depicted plurality of augmented event codes may embody a more holistic view of the event codes relevant to accurately determining an event complexity for a particular event data object than merely the event codes for the primary service encoding 402 or the secondary service encoding alone. In some embodiments, augmented event codes are identified and/or used for performing predicted risk-aware complexity determinations associated with a secondary service encoding. In some embodiments, augmented event codes are identified and/or used for performing predicted risk-aware complexity determinations associated with a primary service encoding. In yet some other embodiments, augmented event codes are identified and/or used for performing predicted risk-aware complexity determinations associated with all service encodings corresponding to a particular event data object, for example for processing of a primary service encoding and a secondary service encoding associated with the same event data object. In one example context, augmented event codes are used to perform complexity determinations for a particular event data object representing a particular medical encounter.

In some embodiments, a new data object is generated comprising at least the plurality of augmented event codes 502. Additionally or alternatively, in some embodiments, the new data object comprising the augmented event codes 502 further includes one or more additional data properties composited from one or more service encoding(s), a participant history profile, and/or the like. For example, in some embodiments, the data object embodying or including the plurality of augmented event codes 502 includes additional information associated with an event entity, time of service information, and/or the like.

In some embodiments, plurality of the augmented event codes 502 is generated by augmenting the event code set 462 associated with the secondary service encoding 452 with the event code set associated with the event code set 412 associated with the primary service encoding 402. The a resulting plurality of augmented event codes 502 may thus embody a combined set of the event codes from each of the primary service encoding 402 and the secondary service encoding 452. In this regard, the plurality of augmented event codes 502 includes both the primary event codes and the secondary event codes. It should be appreciated that in other embodiments, a plurality of augmented event codes may be identified from any number of additional service encoding(s) similarly received. For example, the plurality of augmented event codes 502 may be further augmented to include the event codes of a third service encoding (not depicted) that is similarly determined as associated with the same event data object as the primary service encoding 402 and the secondary service encoding 452. The plurality of augmented event codes 502 may subsequently be processed, as described herein, to more accurately determine an event complexity for the event data object.

In some embodiments, the plurality of augmented event codes 502 is generated in no particular defined order. Alternatively or additionally, in some embodiments, the order of the plurality of augmented event codes 502 is determined based at least in part on the order of the event codes in the source data objects. For example, in some embodiments, the event codes of the primary service encoding 402 are arranged before the event codes of any secondary service encoding, such as the secondary service encoding 452. Alternatively or additionally, in some embodiments, the event codes of the primary service encoding 402 are arranged in an intertwined manner with the event codes of the secondary service encoding 452 (e.g., first event code of the primary service encoding 402, then first event code of the secondary service encoding 452, then second event code of the primary service encoding 402, then second event code of the secondary service encoding 452, and so on). Alternatively or additionally, in some embodiments, the augmented event codes 502 may be pre-processed to determine the order of such event codes, for example based at least in part on a classification determined for each event code. In this regard, it should be appreciated that in contexts where the order of event codes is relevant for processing such event codes, the order of event codes may be maintained as desired during generation of the augmented event codes 502.

In some embodiments, a plurality of augmented event codes is identified based at least in part on a participant history profile. The participant history profile may be utilized to augment a single service encoding, or may be utilized to augment event codes associated with a plurality of service encodings. FIG. 6 illustrates an example visualization of generation of augmented event codes from a service encoding and a participant history profile in accordance with at least some example embodiments of the present disclosure. Specifically, FIG. 6 depicts augmentation of event codes associated with a single service encoding 602 based at least in part on a participant history profile 612. As illustrated, the service encoding 602 includes the same data properties as the primary service encoding as depicted and described with respect to FIG. 4. Thus, for purposes of brevity and clarity of the disclosure, repeated discussion of these data properties individually is omitted.

The participant history profile 612 may include various historical data associated with a particular event entity. For example, in some embodiments the participant history profile 612 includes historical event codes received and/or processed associated with a particular event entity. Alternatively or additionally, in some embodiments, the participant history profile 612 may include all service encoding(s) previously received and/or processed associated with a particular event entity. In this regard, each participant history profile may include comprehensive data associated with a particular event entity, event code(s) associated therewith, and/or the like. As depicted, the participant history profile 612 includes event entity data 614 identifying a particular event entity associated with the participant history profile, and an event code set 616 including any number of historical event codes representing historically received and/or processed event codes associated with the particular event entity. In some embodiments, one or more particular historical event codes from the participant history profile 612 are identified that are associated with or similar to a particular subject matter designation determined for the event corresponding to the service encoding 602.

As illustrated, the service encoding 602 includes the event entity data 604. Such event entity data 604 may uniquely identify a particular event entity for purposes of processing via the complexity processing apparatus 200, for example. In this regard, the complexity processing apparatus 200 may utilize the event entity data 604 to identify a participant history profile 612 associated with said event entity. In this regard, the complexity processing apparatus 200 may query a database that stores the participant history profiles associated with various event entities. The complexity processing apparatus 200 may maintain such a database and/or access an external database that is updated upon receiving and/or processing particular service encoding(s), event data object(s), and/or event code(s) associated therewith.

The complexity processing apparatus 200 generates the augmented event codes 652 from the service encoding 602 and the participant history profile 612. As depicted, the augmented event codes 652 includes the event codes 606 from the service encoding 602 augmented based at least in part on the event code set 616 of the participant history profile 612. In this regard, the plurality of augmented event codes 652 represents a combination of the event codes 606 and 616. The augmented event codes 652 provides a more comprehensive data set associated with a particular event data object based at least in part on the historical data for the event entity corresponding to the event data object to be processed. As such, event code(s) from the event code set 616 associated with the participant history profile 612 that contribute to the complexity of a particular event data object may be identified and processed. Such augmentation may be performed in addition to augmentation of any combination of newly received service encoding(s) (e.g., augmentation of event codes for primary and secondary service encodings). In some embodiments, the participant history profile 612 includes services performed timestamps associated with previously performed services (e.g., corresponding to the historical event codes), servicing entity identifiers for the servicing entities having performed such services, and/or the like.

FIG. 7 illustrates an example visualization of code-wise risk score and code-wise complexity designation generation in accordance with yet some example embodiments of the present disclosure. Specifically, FIG. 7 depicts generation of code-wise risk scores and code-wise complexity designations for each of a plurality of augmented event codes 702. It should be appreciated that such generation may be performed by a complexity processing apparatus 200 upon identification of such augmented event codes 702. For example, the augmented event codes 702 may be identified from a plurality of service encoding(s), as described herein with respect to FIG. 5 for example, and/or a participant history profile, as described herein with respect to FIG. 6 for example.

As illustrated, each of the plurality of augmented event codes 702 is processed to generate a corresponding code-wise risk score of the set of code-wise risk scores 706. The code-wise risk score may describe a measure of the contribution of the augmented event code to a higher event complexity for a particular event data object. As illustrated, for example, a code-wise risk score closer to 1.0 may indicate a higher contribution of a particular augmented event code towards a high event complexity, whereas a code-wise risk score closer to 0.0 may indicate a lower contribution of a particular augmented event code towards a high event complexity. It should be appreciated that, in other embodiments, another scale may be utilized for representing code-wise risk scores, for example from 0 to 100 and/or the like. In some embodiments, each augmented event code corresponds to a predetermined code-wise risk score, for example determined from a database, lookup table, and/or the like. In this regard, the code-wise risk score may be generated utilizing a lookup operation to identify the corresponding predetermined code-wise risk score.

Alternatively or additionally, in some embodiments, each augmented event code of the plurality of augmented event codes 702 is applied to a code scoring model 704 to generate the corresponding code-wise risk score of the set of code-wise risk scores 706. The code scoring model 704 may embody a statistical, algorithmic, and/or machine learning model, or a combination thereof, that accurately generates a code-wise risk score based at least in part on an inputted augmented event code (or set of augmented event codes). In some embodiments, the code scoring model 704 embodies a specially trained machine learning model that generates the code-wise risk score based at least in part on the inputted augmented event code(s). For example, in some embodiments, the machine learning model is trained utilizing a supervised learning method, such as based at least in part on training data including event codes and corresponding code-wise risk scores. Alternatively or additionally, in some embodiments, the machine learning model is trained utilizing an unsupervised learning method, such that the machine learning model learns the augmented event codes that most contribute to high event complexities. In some other embodiments, the code scoring model 704 embodies an algorithm that maintains a mapping between augmented event codes and corresponding predetermined code-wise risk scores.

Each code-wise risk score may be utilized to determine a predefined complexity category associated with the augmented event code. In some embodiments, the complexity processing apparatus 200 maintains a mapping between the code-wise risk scores and each predefined complexity category of a set of possible predefined complexity categories. For example, as illustrated the complexity processing apparatus 200 may be associated with the predefined complexity categories 752, 754, 756, 758, and 760. Each of these predefined complexity categories is maintained associated with a particular range of code-wise risk scores that correspond to the particular predefined complexity category. For example, as illustrated, code-wise risk scores falling within the range of 0.0 and 0.20 are associated with a "low" predefined complexity category (e.g., indicating low event complexity), code-wise risk scores falling within the range of 0.21 to 0.40 are associated with a "moderate-low" predefined complexity category, code-wise risk scores falling within the range of 0.41 to 0.70 are associated with a "moderate" predefined complexity category, code-wise risk scores falling within the range of 0.71 to 0.90 are associated with a "moderate-high" predefined complexity category, and code-wise risk scores falling within the range of 0.91 to 1.0 are associated with a "high" predefined complexity category (e.g., indicating high event complexity). In some such embodiments, the complexity processing apparatus 200 may apply each code-wise risk score of the set of code-wise risk scores 706 to the possible predefined complexity categories to determine the corresponding predefined complexity category for the associated augmented event code. For example, as illustrated, the first augmented event code of the plurality of augmented event codes 702 is associated with a code-wise risk score of 0.21, and thus would be determined as associated with the "moderate-low" predefined complexity category 754. Alternatively, the second augmented event code of the plurality of augmented event codes 702 is associated with a code-wise risk score of 0.45 and thus would be determined as associated with the "moderate" predefined complexity category 756. The complexity processing apparatus 200 may iteratively determine the predefined complexity category corresponding to each of the plurality of augmented event codes 702 based at least in part on the corresponding code-wise risk score of the set of code-wise risk scores 706 accordingly. In some embodiments, each code-wise risk score of the code-wise risk scores 706 is used to generate a corresponding weight (e.g., representing a second and/or converted code-wise risk score) that is usable to generate an event complexity determination, and/or is combinable with one or more other weights to generate an event complexity determination. In some embodiments a weight corresponding to and/or representing a code-wise risk score (or an algorithmic transformation associated with a combination of code-wise risk scores) is utilized to generate and/or otherwise determine an event complexity determination, as described herein with respect to FIGS. 8 and 9 for example.

FIG. 8 illustrates an example visualization of intensive risk subset generation and risk-based complexity score generation in accordance with at least some example embodiments of the present disclosure. Specifically, FIG. 8 depicts an identified intensive risk subset 802 of the plurality of augmented event codes 702 as depicted and described with respect to FIG. 7, and a risk-based complexity score 806 generated associated therewith. As depicted, the intensive risk subset 802 includes only two augmented event codes. In some such embodiments, for example, the complexity processing apparatus 200 may identify the augmented event codes associated with the highest code-wise risk scores of all augmented event codes. In this regard, the augmented event codes of the intensive risk subset 802 are associated with the code-wise risk scores 804 of 0.91 and 0.71—the two highest code-wise risk scores of the set of code-wise risk scores 706. It should be appreciated that the particular intensive risk subset 802 is an example and, in other embodiments, a different intensive risk subset may be identified utilizing a different process. For example, in some other embodiments, the intensive risk subset is identified based at least in part on the augmented event codes associated with the top 5 highest code-wise risk scores. Alternatively, in some other embodiments for example, the intensive risk subset is identified based at least in part on the augmented event codes associated with the top 10% highest code-wise risk scores.

In some embodiments, the complexity processing apparatus 200 generates a risk-based complexity score 806 based at least in part on the augmented event codes of the intensive risk subset 802. Specifically, in some embodiments, the complexity processing apparatus 200 processes the code-wise risk scores 804 associated with the augmented event codes of the intensive risk subset 802 to generate the risk-based complexity score 806 therefrom. In some embodiments, the complexity processing apparatus 200 generates the risk-based complexity score 806 by transforming the code-wise risk scores 804 utilizing one or more algorithm(s), model(s), and/or the like. In some embodiments, for example, the complexity processing apparatus 200 generates the risk-based complexity score 806 by performing a weighted average of the code-wise risk scores 804 for the augmented event codes represented in the intensive risk subset 802. The weights may be predetermined, determined based at least in part on the rank order of the code-wise risk scores (e.g., highest scoring code-wise risk score associated with the highest weight, second highest associated with the second highest wright, and so on), and/or manually configurable. Alternatively or additionally, in some embodiments, the risk-based complexity score 806 is generated utilizing a simple average of the code-wise risk scores 804 for the augmented event codes of the intensive risk subset 802. In yet other embodiments, any other determinable algorithmic transformation may be applied to the code-wise risk scores 804 to generate the risk-based complexity score 806.

In some embodiments, the risk-based complexity score 806 is utilized to determine a particular predefined complexity category based at least in part on the intensive risk subset 802. For example, in some embodiments, the complexity processing apparatus 200 may apply the risk-based complexity score 806 to the possible predefined complexity categories 752, 754, 756, 758, and 760 to determine the corresponding predefined complexity category for the event data object overall based at least in part on the intensive risk subset 802. For example, as illustrated, the risk-based complexity score 806 is generated with the value of 0.81, and thus would be determined as associated with the "moderate-high" predefined complexity category 758. In this regard, the event complexity associated with the event data object based at least in part on the intensive risk subset may similarly represent the "moderate-high" predefined complexity category 758. The risk-based complexity score 806 and/or predefined complexity category associated therewith may be processed as-is, or utilized to generate and/or determine a corresponding weight for further processing. For example, in some embodiments the risk-based complexity score 806 embodies or is converted into a weight utilized to generate an event complexity determination in conjunction with weight represented by a category-based complexity score described herein. By processing the intensive risk subset, embodiments of the present disclosure accurately determine such complexity categorizations based at least in part on the augmented event codes that most contribute to the highest event complexity. Thus, such embodiments may more accurately predict an event complexity (e.g., associated with the predefined complexity category predicted from the risk-based complexity score) in circumstances where the highest contributing augmented event codes support a particular predicted event complexity, and may more accurately determine whether a predicted event complexity matches a submitted event complexity for a particular event data object.

FIG. 9 illustrates an example visualization of category-based complexity score generation in accordance with at least some example embodiments of the present disclosure. Specifically, FIG. 9 depicts generation of an category-based complexity score 904 from a set of code-wise risk scores 706 for a set of augmented event codes 702. In this regard, the category-based complexity score 904 may correspond to a determined event complexity for the event data object associated with all the plurality of augmented event codes 702 corresponding to said event data object.

In some embodiments, the complexity processing apparatus 200 generates the category-based complexity score 904 by transforming the set of code-wise risk scores 706 utilizing one or more algorithm(s), model(s), and/or the like. In some embodiments, for example, the complexity processing apparatus 200 generates the category-based complexity score 904 by performing a weighted average of the code-wise risk scores 706, a simple average of the code-wise risk scores 706, and/or the like. In some such embodiments, additionally or alternatively, the code-wise risk scores 706 are used to generate intermediary weights for each augmented event code (e.g., generated by a predefined weighting algorithm), which are then used to generate the corresponding category-based complexity score 904 (e.g., via a weighted average or other algorithm). Alternatively or additionally, in some embodiments, the category-based complexity score 904 is generated based at least in part on a combination of code-wise risk score(s) that satisfy a particular minimum score threshold. In yet other embodiments, any other determinable algorithmic transformation may be applied to the code-wise risk scores 706 to generate the category-based complexity score 904.

In some embodiments, the category-based complexity score 904 is utilized to determine a particular predefined complexity category based at least in part on all event codes represented in the plurality of augmented event codes 702. For example, in some embodiments, the complexity processing apparatus 200 may apply the category-based complexity score 904 to the possible predefined complexity categories 752, 754, 756, 758, and 760 to determine the corresponding predefined complexity category for the event data object overall based at least in part on the full plurality of augmented event codes 702. For example, as illustrated, the category-based complexity score 904 is generated with the value of 0.92, and thus would be determined as associated with the "high" predefined complexity category 760. In this regard, the event complexity associated with the event data object based at least in part on the full plurality of augmented event codes 702 may similarly represent the "high" predefined complexity category 760. By processing the full plurality of augmented evet codes, embodiments of the present disclosure accurately determine such a complexity categorization based at least in part on the combination of contributions from all augmented event codes affecting the event complexity of the event data object. For example, in circumstances where all augmented event codes include a threshold number of moderate and/or moderate-high complexity augmented event codes that contribute to the event complexity for the event data object, the category-based complexity score 904 may reflect an increased complexity based at least in part on the contributions from the combination of augmented event codes. The category-based complexity score 904 and/or predefined complexity category associated therewith may be processed as-is, or utilized to generate and/or determine a corresponding weight for further processing (e.g., to generate an event complexity determination). For example, in some embodiments the category-based complexity score 904 embodies or is converted into a weight utilized to generate an event complexity determination in conjunction with weight represented by a risk-based complexity score described herein.

In some embodiments, the risk-based complexity score based at least in part on an intensive risk subset and the category-based complexity score based at least in part on the full plurality of augmented risk scores are determined for a particular event data object. The complexity processing apparatus 200 may determine a predefined complexity category predicted and/or otherwise assigned to an event data object based at least in part on the risk-based complexity score and the category-based complexity score generated for said event data object. For example, the complexity processing apparatus 200 may compare the risk-based complexity score and the category-based complexity score, and determine the predefined complexity category representing the event complexity based at least in part on the higher of the two complexity scores. In other embodiments, the complexity processing apparatus 200 may utilize a combination of the category-based complexity score and the risk-based complexity score to generate a combined score corresponding to the predicted event complexity for the event data object, as described herein.

Example Processes of the Disclosure

Having described example systems, apparatuses, contexts, data visualizations, and computing contexts in accordance with the present disclosure, example processes of the present disclosure will now be described. It will be appreciated that each of the flowcharts depicts an example computer-implemented process that may be performed by one or more of the apparatuses, systems, devices, and/or computer program products described herein, for example, utilizing one or more of the specially configured components thereof.

The blocks depicted indicate operations of each process. Such operations may be performed in any of a number of ways, including, without limitation, in the order and manner as depicted and described herein. In some embodiments, one or more blocks of any of the processes described herein occur in-between one or more blocks of another process, before one or more blocks of another process, in parallel with one or more blocks of another process, and/or as a sub-process of a second process. Additionally or alternatively, any of the processes may include some or all operational steps described and/or depicted, including one or more optional blocks in some embodiments. With regard to the flowcharts illustrated herein, one or more of the depicted blocks may be optional in some, or all, embodiments of the disclosure. Optional blocks are depicted with broken (or "dashed") lines. Similarly, it should be appreciated that one or more of the operations of each flowchart may be combinable, replaceable, and/or otherwise altered as described herein.

FIG. 10 illustrates a flowchart including example operations of an example process for performing a predicted risk-aware complexity determination for an event data object utilizing a plurality of augmented event codes in accordance with at least some example embodiments of the present disclosure. Specifically, FIG. 10 depicts operations of an example process 1000. In some embodiments, the process 1000 is embodied by computer program code stored on a non-transitory computer-readable storage medium of a computer program product configured for execution to perform the process as depicted and described. Alternatively or additionally, in some embodiments, the process 1000 is performed by one or more specially configured computing devices, such as the complexity processing apparatus 200 alone or in communication with one or more other component(s), device(s), system(s), and/or the like. In this regard, in some such embodiments, the complexity processing apparatus 200 is specially configured by computer-coded instructions (e.g., computer program instructions) stored thereon, for example in the memory 204 and/or another component depicted and/or described herein and/or otherwise accessible to the complexity processing apparatus 200, for performing the operations as depicted and described. In some embodiments, the complexity processing apparatus 200 is in communication with one or more external apparatus(es), system(s), device(s), and/or the like, to perform one or more of the operations as depicted and described. For example, the complexity processing apparatus 200 may be in communication with a client device and/or external data system. For purposes of simplifying the description, the process 1000 is described as performed by and from the perspective of the complexity processing apparatus 200.

The process 1000 begins at optional operation 1002. At optional operation 1002, the complexity processing apparatus 200 includes means, such as the scores processing circuitry 212, the code augmentation circuitry 210, the communications circuitry 208, the input/output circuitry 206, the processor 202, and/or the like, or a combination thereof, to receive one or more service encoding(s) corresponding to an event data object. In some embodiments, the service encoding(s) may be received from one or more external encoding submission systems in communication with the complexity processing apparatus 200. For example, the service encoding(s) may be received upon submission of said service encodings to the one or more external encoding submission systems in response to the event data object.

The service encoding(s) may each include any number of event codes associated with the event data object. In some embodiments, the complexity processing apparatus 200 receives one service encoding for processing. Alternatively or additionally, in some embodiments, the complexity processing apparatus 200 receives a plurality of service encodings, each associated with the same event data object. For example, in some embodiments, the complexity processing apparatus 200 receives a primary service encoding and a secondary service encoding associated with the same event data object.

At operation 1004, the complexity processing apparatus 200 includes means, such as circuitry 208, the input/output circuitry 206, the processor 202, and/or the like, or a combination thereof, to identify a plurality of augmented event codes for an event data object. In some embodiments, the plurality of augmented event codes are identified from one or more received service encodings. For example, in some embodiments, the plurality of augmented event codes are identified from extracting the event codes from a first service encoding and utilizing the extracted event codes to augment the set of event codes included in the second service encoding. In some such embodiments, the plurality of augmented event codes includes the combination of event codes from each of the received service encodings.

Alternatively or additionally, in some embodiments, the received event codes (e.g., event codes in a single received service encoding) are augmented based at least in part on identifiable historical event codes. In some embodiments, for example, the complexity processing apparatus 200 retrieves a participant history profile that includes the historical event codes to be utilized in identifying the plurality of augmented event codes. The participant history profile may be associated with the same event entity as the received event codes. For example, in some embodiments the complexity processing apparatus 200 determines an event entity identifier from a service encoding including the event codes, and queries one or more data repositories storing historical data for the participant history profile based at least in part on the event entity identifier. In this regard, the historical participant profile may include event codes associated the same event entity, and that were associated with previously received and/or processed event data objects. In this regard, such historical event codes may provide relevant context that enables more accurate scoring and/or determinations then just received event codes alone.

In some embodiments, by augmenting event codes for an event data object before performing predictive data analysis operations on the event codes, a proposed solution increases the likelihood that predictive data analysis operations performed on event data objects are performed on complete and correct event codes for the noted event data objects, thus decreasing the need for performing predictive data analysis operations on event data objects again after failed initial attempts to perform predictive data analysis operations on event data objects. This in turn decreases the operational load on predictive data analysis frameworks that are configured to perform predictive data analysis operations on event data objects and increases the computational efficiency as well as the operational reliability of the noted predictive data analysis frameworks. In this way, various embodiments of the present invention make important technical contributions to the fields of predictive data analysis and event processing.

Moreover, by processing the event codes that remain unverified with respect to completeness and/or comprehensiveness, and performing a determination based at least in part on such unverified or untrustworthy event codes, the data system may produce resulting data via such determinations that is inaccurate. In circumstances where the data system initiates and/or performs one or more additional process(es) based at least in part on the results of such determinations, the inaccurate resulting data may further cause the data system to wrongly initiate a process and/or initiate the wrong process. In this regard, the accuracy of the resulting data produced by the data system suffers from processing the unverified and/or untrustworthy event codes. Furthermore, resources (including, without limitation: networking resources, processing resources, memory resources, and/or valuable resources) may be entirely wasted by wrongly initiating one or more process(es) based at least in part on inaccurate resulting data from such a determination. In some contexts, one or more process(es) initiated based at least in part on inaccurate data resulting from such determination(s) that utilized unverified and/or untrustworthy data may entirely degrade the data system by taking up all resources of the data system, triggering an irreversible action, and/or the like.

At operation 1006, the complexity processing apparatus 200 includes means, such as the scores processing circuitry 212, the code augmentation circuitry 210, the communications circuitry 208, the input/output circuitry 206, the processor 202, and/or the like, or a combination thereof, to determine whether an augmented event code of the augmented event code remains unprocessed. In some embodiments, the complexity processing apparatus 200 iteratively processes each augmented event code in the plurality of augmented event codes, such that the complexity processing apparatus 200 tracks and/or may otherwise determines at any time which augmented event codes have yet to be processed. In some embodiments, the plurality of augmented event codes are stored in a data structure that enables iterating through the plurality of augmented event codes in a particular order (e.g., based at least in part on index). Should the complexity processing apparatus 200 determine a next augmented event code remains unprocessed, the complexity processing apparatus 200 may proceed to process the next augmented event code and flow proceeds to operation 1008. In a circumstance where the complexity processing apparatus 200 determines a next augmented event code does not exist (e.g., all augmented event codes have been processed), the complexity processing apparatus may continue operations and flow proceeds to operation 1012.

At operation 1008, the complexity processing apparatus 200 includes means, such as the scores processing circuitry 212, the code augmentation circuitry 210, the communications circuitry 208, the input/output circuitry 206, the processor 202, and/or the like, or a combination thereof, to, for a particular augmented event code currently being processed, determine a code-wise risk score. In some embodiments, the code-wise risk score describes a measure of contribution of the augmented event code to an event complexity of the event data object. In some embodiments, the complexity processing apparatus 200 stores a mapping of each event code to a code-wise risk score. It will be appreciated that, in other embodiments, the code-wise risk score is determined based at least in part on determining a relationship between a combination of event codes, for example where the combination is mapped to a particular code-wise risk score. Alternatively or additionally, in some embodiments, the complexity processing apparatus 200 utilizes a model specially tuned to generate the code-wise risk score for a particular inputted augmented event code.

At operation 1010, the complexity processing apparatus 200 includes means, such as the scores processing circuitry 212, the code augmentation circuitry 210, the communications circuitry 208, the input/output circuitry 206, the processor 202, and/or the like, or a combination thereof, to, for a particular augmented event code currently being processed, determine a code-wise complexity designation. In some embodiments, the code-wise complexity designation describes whether the augmented event code is associated with a predefined complexity category. The code-wise complexity designation may be determined based at least in part on the value of the code-wise complexity score for the augmented event code. For example, in some embodiments, the complexity processing apparatus 200 maintains a range of code-wise complexity scores associated with each code-wise complexity designation. Alternatively or additionally, in some embodiments, the complexity processing apparatus 200 utilizes one or more model(s) specially tuned to determine the code-wise complexity designation, for example based at least in part on the inputted code-wise risk score.

At operation 1012, the complexity processing apparatus 200 includes means, such as circuitry 208, the input/output circuitry 206, the processor 202, and/or the like, or a combination thereof, to determine a risk-based complexity score for the event data object. In some embodiments, the risk-based complexity score is determined based at least in part on each code-wise risk score for an intensive risk subset. In some embodiments, the complexity processing apparatus 200 includes means, such as the scores processing circuitry 212, the code augmentation circuitry 210, the communications circuitry 208, the input/output circuitry 206, the processor 202, and/or the like, or a combination thereof, to identify the intensive risk subset. The intensive risk subset may be determined based at least in part on each code-wise risk score for the plurality of augmented event codes. For example, in some embodiments, the complexity processing apparatus 200 determines the intensive risk subset by identifying a determinable number of the augmented event codes associated with the highest code-wise risk scores (e.g., top two scoring augmented event codes, top five augmented event codes, top 10 percent augmented event codes, and/or the like). The size of the intensive risk subset may be determined based at least in part on results from a statistical analysis of event codes in a particular context, for example utilized to determine a size at which addition of subsequent augmented event codes does not further increase the accuracy of the corresponding determination above a minimum improvement threshold. Alternatively or additionally, in some embodiments, the intensive risk subset is processed to determine a particular code-wise risk score based on the individual event codes of the intensive risk subset and/or relationship(s) between said event codes.

The risk-based complexity score may be determined utilizing one or more algorithm(s), model(s), and/or other transformations based at least in part on the code-wise risk scores and/or code-wise complexity designation for each augmented event code in the intensive risk subset. For example, in some embodiments, the complexity processing apparatus 200 determines a risk-based complexity score corresponding to the highest complexity designation of the code-wise complexity designations for the augmented event code of the intensive risk subset. Alternatively or additionally, in some embodiments, the risk-based complexity score may be determined by applying the code-wise risk scores corresponding to the intensive risk subset to a determinable risk-based complexity score determination algorithm. Each event code may be mapped to a particular risk level that corresponds to a weight representing the corresponding code-wise risk score. The risk-based complexity score determination algorithm may transform the code-wise risk scores utilizing a weighted-average algorithm, for example with the weight for each code-wise risk score determined based at least in part on the code-wise complexity designation associated with the augmented event code, determinations derived therefrom, and/or the like. Alternatively or additionally in some embodiments, the complexity processing apparatus 200 determines the risk-based complexity score utilizing an averaging algorithm to process the code-wise risk score for the augmented event codes. It should be appreciated that the complexity processing apparatus 200 may implement any risk-based complexity score determination algorithm that determines the risk-based complexity score from data associated with each augmented event code of the plurality of augmented event codes.

At operation 1014, the complexity processing apparatus 200 includes means, such as the scores processing circuitry 212, the code augmentation circuitry 210, the communications circuitry 208, the input/output circuitry 206, the processor 202, and/or the like, or a combination thereof, to determine a category-based complexity score for the event data object. In some embodiments, the category-based complexity score is determined based at least in part on each code-wise complexity designation for the plurality of augmented event codes. For example, in some embodiments, the complexity processing apparatus 200 determines a number of code-wise complexity designations that satisfy a high-complexity threshold, and determines whether the number of code-wise complexity designations satisfies a minimum threshold number of high-complexity event codes. Alternatively or additionally, in some embodiments, the complexity processing apparatus 200 processes the code-wise complexity designation to perform any determination that determines whether the code-wise complexity designations for each of the plurality of augmented event codes contribute to a higher complexity designation in combination.

At operation 1016, the complexity processing apparatus 200 includes means, such as the scores processing circuitry 212, the code augmentation circuitry 210, the communications circuitry 208, the input/output circuitry 206, the processor 202, and/or the like, or a combination thereof, to generate the predicted risk-aware complexity determination based at least in part on the risk-based complexity score and the category-based complexity score. In some embodiments, the complexity processing apparatus 200 generates a complexity determination corresponding to each of the risk-based complexity score and the category-based complexity score. The complexity processing apparatus 200 may generate the predicted risk-aware complexity determination that represents the higher complexity between the complexity designation for the risk-based complexity score and the complexity designation for the category-based complexity score. Alternatively or additionally, in some embodiments, the predicted-risk aware complexity determination is generated based at least in part on a combination of the risk-based complexity score and the category-based complexity score. For example, in some embodiments, the complexity processing apparatus averages and/or otherwise transforms the risk-based complexity score and the category-based complexity score to generate a combined complexity score, and determines the predicted risk-aware complexity determination corresponding to the combined complexity score.

In one example context, the risk-based complexity score and the category-based complexity score each represent a different weight contributing towards medical complexity. For example, the risk-based complexity score may indicate a weight contributed to event complexity (e.g., a level of medical decision making to be performed during a particular medical encounter) by the highest complexity event code(s) of the augmented event codes, whereas the category-based complexity score may represent a weight contributed to event complexity by the combination of all of the augmented event codes. In one particular example, a first service encoding for which event complexity is to be determined (e.g., a professional claim) includes a single procedure code and three diagnosis codes, thus totaling 4 event codes. The first service encoding may include a first event code (e.g., the procedure code) determined as associated with a particular high complexity designation, for example 99285 indicating a high level of medical decision making during emergency depart evaluation of a patient. The first service encoding may be augmented based at least in part on a second service encoding (e.g., a facility claim) associated with the same event data object, for example where the second service encoding includes two procedure codes and five diagnosis codes, thus totaling 7 event codes for the second service encoding and 12 augmented event codes. The second service encoding may include other event codes determined as associated with other complexity designations, for example R05 diagnosis code associated with lower complexity of medical decision making.

A weight (e.g., represented by a code-wise risk score) may be determined for each of the diagnosis codes embodied in the augmented event codes and/or a combination of the event codes. For example, the diagnosis codes contributed from the first service encoding may each be determined to be associated with code-wise risk scores that represent their contribution towards an event complexity alone or in combination with other augmented event codes. The first diagnosis code from the first service encoding may be associated with a code-wise risk score of 100, the second diagnosis code from the first service encoding may be associated with a code-wise risk score of 300, and the third diagnosis code from the first service encoding may be associated with a code-wise risk score of 0. The first diagnosis code from the second service encoding may be associated with a code-wise risk score of 300, the second diagnosis code from the second service encoding may be associated with a code-wise risk score of 330, the third diagnosis code from the second service encoding may be associated with a code-wise risk score of 200, the fourth diagnosis code from the second service encoding may be associated with a code-wise risk score of 200, and the fifth diagnosis code from the second service encoding may be associated with a code-wise risk score of 200. In this regard, by processing the augmented event codes corresponding to diagnosis codes of the received service encodings, a total of 7 separate event codes contribute a weight towards the event complexity determination. In this regard, the risk-based complexity score may embody an aggregate (or other algorithmically determined) value of the weights of each of the individually contributing event codes of the set of augmented event codes or a particular subset thereof (e.g., an intensive risk subset). Similarly, the category-based complexity score may embody an additional weight based on the number of augmented event codes contributing a weight (or in other embodiments, at least a minimum weight) towards the event complexity, or based on the number of augmented event codes satisfying a particular threshold number of event codes contributing towards event complexity regardless of the individual complexity of each event code. For example, in some embodiments, an additional weight embodied by the category-based complexity score determined in a circumstance where a certain number of contributing event codes are present in the augmented event codes increases as the number of contributing event codes increases (e.g., 7 contributing event codes is associated with a lower category-based complexity score than 8 contributing event codes, and so on).

At optional operation 1018, the complexity processing apparatus 200 includes means, such as the scores processing circuitry 212, the code augmentation circuitry 210, the communications circuitry 208, the input/output circuitry 206, the processor 202, and/or the like, or a combination thereof, to perform one or more prediction-based actions based at least in part on the predicted risk-aware complexity determination. In some embodiments, the complexity processing apparatus 200 determines whether the predicted risk-aware complexity determination satisfies (e.g., meets or exceeds) a particular complexity designation. For example, in some embodiments, the complexity processing apparatus 200 compares the predicted risk-aware complexity determination with a submitted complexity designation associated with one or more received service encoding(s). The complexity processing apparatus 200 may perform a particular prediction-based action based at least in part on the results of the comparison. For example, in some embodiments, the complexity processing apparatus 200 initiates a prediction-based action that approves processing of a received service encoding in a circumstance where the predicted risk-aware complexity determination satisfies a submitted complexity designation associated with the service encoding, initiates a prediction-based action that denies processing of the received service encoding in a circumstance where the predicted risk-aware complexity determination does not satisfy the submitted complexity designation associated with the service encoding, and/or the like.

In one example context, the event data object corresponds to service encoding(s) embodying submitted claims for services performed during a medical encounter. The predicted risk-aware complexity determination may represent a predefined complexity categorization for the event data object corresponding to such claims, which is more accurately generated based at least in part on use of the augmented event codes from the service encodings, participant history profile, and/or the like. As such, the event complexity corresponding to the event data object may be utilized to perform an appropriate processing action for the claims embodied by the service encodings associated therewith. For example, the prediction-based action may include initiating process of the claim with the requested claim amount (e.g., in a circumstance where the predicted event complexity represented by the predicted risk-aware complexity determination exceeds or meets the submitted event complexity received with the service encoding), initiate processing of the claim with an adjusted claim amount (e.g., in a circumstance where the predicted event complexity represented by the predicted risk-aware complexity determination is near but does not meet the submitted event complexity received with the service encoding), and/or denying processing of the claim (e.g., in a circumstance where the predicted event complexity does not meet and/or is not close to the submitted event complexity). In this regard, it should be appreciated that such embodiments more accurately perform the prediction-based actions based at least in part on the increased accuracy of the resulting predicted risk-aware complexity determinations.

FIG. 11 illustrates a flowchart including example operations of another example process for determining a category-based complexity score in accordance with at least some example embodiments of the present disclosure. Specifically, FIG. 11 depicts operations of an example process 1100. In some embodiments, the process 1100 is embodied by computer program code stored on a non-transitory computer-readable storage medium of a computer program product configured for execution to perform the process as depicted and described. Alternatively or additionally, in some embodiments, the process 1100 is performed by one or more specially configured computing devices, such as the complexity processing apparatus 200 alone or in communication with one or more other component(s), device(s), system(s), and/or the like. In this regard, in some such embodiments, the complexity processing apparatus 200 is specially configured by computer-coded instructions (e.g., computer program instructions) stored thereon, for example in the memory 204 and/or another component depicted and/or described herein and/or otherwise accessible to the complexity processing apparatus 200, for performing the operations as depicted and described. In some embodiments, the complexity processing apparatus 200 is in communication with one or more external apparatus(es), system(s), device(s), and/or the like, to perform one or more of the operations as depicted and described. For purposes of simplifying the description, the process 1100 is described as performed by and from the perspective of the complexity processing apparatus 200.

The process 1100 begins at operation 1102. In some embodiments, the process 1100 begins after one or more operations depicted and/or described with respect to any of the other processes described herein. For example, in some embodiments as depicted, the process 1100 begins after execution of operation 1012. In this regard, some or all of the process 1100 may replace or supplement one or more blocks depicted and/or described with respect to any of the other processes described herein, such as the operation 1014. Upon completion of the process 1100, the flow of operations may terminate. Additionally or alternatively, as depicted, upon completion of the process 1100, flow may return to one or more operations of another process, such as the operation 1016. It should be appreciated that, in some embodiments, the process 1100 embodies a subprocess of one or more other process(es), such as the process 1000.

At operation 1102, the complexity processing apparatus 200 includes means, such as circuitry 208, the input/output circuitry 206, the processor 202, and/or the like, or a combination thereof, to determine a selected subset of the plurality of augmented event codes having affirmative code-wise complexity designations. In some embodiments, the affirmative code-wise designations embody each code-wise complexity designation that satisfies a minimum complexity designation threshold. The minimum complexity designation threshold may be predetermined, identified based at least in part on one or more determinations by the complexity processing apparatus 200, and/or the like. For example, in some embodiments, the complexity processing apparatus 200 determines the minimum complexity designation threshold based at least in part on a submitted complexity for a received service encoding.

At operation 1104, the complexity processing apparatus 200 includes means, such as the scores processing circuitry 212, the code augmentation circuitry 210, the communications circuitry 208, the input/output circuitry 206, the processor 202, and/or the like, or a combination thereof, to determine a size of the selected subset. In this regard, the complexity processing apparatus 200 may determine the number of augmented event codes that were associated with complexities satisfying the minimum complexity designation threshold. In some embodiments, the size of the selected subset indicates a number of augmented event codes that, alone and/or in combination, indicate a higher complexity designation for the event data object.

At operation 1106, the complexity processing apparatus 200 includes means, such as the scores processing circuitry 212, the code augmentation circuitry 210, the communications circuitry 208, the input/output circuitry 206, the processor 202, and/or the like, or a combination thereof, to determine the category-based complexity score based at least in part on whether the size satisfies a size threshold. In some embodiments, the size threshold is predetermined. In other embodiments, the size threshold is determined by the complexity processing apparatus, for example based at least in part on the total number of augmented event codes (e.g., as a percentage of the augmented event codes). In some embodiments, the complexity processing apparatus 200 compares the size of the selected subset with the size threshold to determine the category-based complexity score.

FIG. 12 illustrates a flowchart including example operations of another example process for determining initial complexity condition satisfaction in accordance with at least some example embodiments of the present disclosure. Specifically, FIG. 12 depicts operations of an example process 1200. In some embodiments, the process 1200 is embodied by computer program code stored on a non-transitory computer-readable storage medium of a computer program product configured for execution to perform the process as depicted and described. Alternatively or additionally, in some embodiments, the process 1200 is performed by one or more specially configured computing devices, such as the complexity processing apparatus 200 alone or in communication with one or more other component(s), device(s), system(s), and/or the like. In this regard, in some such embodiments, the complexity processing apparatus 200 is specially configured by computer-coded instructions (e.g., computer program instructions) stored thereon, for example in the memory 204 and/or another component depicted and/or described herein and/or otherwise accessible to the complexity processing apparatus 200, for performing the operations as depicted and described. In some embodiments, the complexity processing apparatus 200 is in communication with one or more external apparatus(es), system(s), device(s), and/or the like, to perform one or more of the operations as depicted and described. For purposes of simplifying the description, the process 1200 is described as performed by and from the perspective of the complexity processing apparatus 200.

The process 1200 begins at operation 1202. In some embodiments, the process 1200 begins after one or more operations depicted and/or described with respect to any of the other processes described herein. For example, as depicted, operation 1202 may begin after operation 1004 as depicted and described with respect to the process 1000. In this regard, some or all of the process 1200 may replace or supplement one or more blocks depicted and/or described with respect to any of the other processes described herein. Upon completion of the process 1200, the flow of operations may terminate. Additionally or alternatively, as depicted, upon completion of the process 1200, flow may return to one or more operations of another process, such as the operation 1006. It should be appreciated that, in some embodiments, the process 1200 embodies a subprocess of one or more other process(es), such as the process 1000.

At operation 1202, the complexity processing apparatus 200 includes means, such as the scores processing circuitry 212, the code augmentation circuitry 210, the communications circuitry 208, the input/output circuitry 206, the processor 202, and/or the like, or a combination thereof, to initiate a determination of whether the event data object satisfies one or more initial complexity conditions. In some embodiments, an initial complexity condition represents a condition that, if satisfied, indicates that the event data object is associated with an event complexity at or above a particular level. The initial complexity condition may include a determination of whether one or more particular event codes are associated with the event data object, for example event code(s) associated with particular predetermined high complexity designations. In some embodiments, the complexity processing apparatus 200 is configured to perform any of a number of determinations that check for satisfaction of initial complexity conditions based at least in part on any of the data associated with the event data object. For example, an initial complexity condition may be satisfied based at least in part on a number of event data code(s), the existence of certain data code(s) associated with the event data object, the existence of certain data codes in a participant history profile associated with the event entity corresponding to a particular event data object, and/or the like. It should be appreciated that the complexity processing apparatus 200 may be configured to perform a determination for any condition relevant to immediately identifying an event complexity. For example, additionally or alternatively in some embodiments, the complexity processing apparatus 200 processes other data associated with the event entity (e.g., age, discharge status, and/or the like), diagnosis information, servicing entity information, claim or bill type information, and/or the like.

At operation 1204, the complexity processing apparatus 200 includes means, such as the scores processing circuitry 212, the code augmentation circuitry 210, the communications circuitry 208, the input/output circuitry 206, the processor 202, and/or the like, or a combination thereof, to determine whether at least one initial complexity condition is satisfied. In some embodiments, in a circumstance where the complexity processing apparatus 200 determines at least one initial complexity condition is satisfied for the event data object, the flow ends. In this regard, the event data object may be associated with a submitted event complexity in a circumstance where such initial complexity condition(s) are satisfied. Such embodiments may advantageously accurately determine an event complexity associated with a particular event data object without expending computing resources for subsequent detailed processing of the event data object and/or data associated therewith for such purposes. It should be appreciated that, in other embodiments, the flow ends in a circumstance where the complexity processing apparatus 200 determines that all initial complexity conditions of a set of initial complexity conditions are met.

As illustrated, in a circumstance where the complexity processing apparatus 200 determines that at least one initial complexity condition is not satisfied, flow proceeds to operation 1002. In this regard, the complexity processing apparatus 200 may determine that the data associated with a particular event data object (e.g., the event codes associated therewith) requires additional processing to determine an accurate event complexity for the event data object. For example, the complexity processing apparatus 200 may proceed to process the event codes associated with the event data object as depicted and described with respect to process 1000. In this regard, the complexity processing apparatus 200 may proceed with processing data associated with the event data object to more accurately determine and/or assign a designation representing an event complexity to the event data object and/or service encoding(s) associated therewith. Moreover, as described above, by augmenting event codes for an event data object before performing predictive data analysis operations on the event codes, a proposed solution increases the likelihood that predictive data analysis operations performed on event data objects are performed on complete and correct event codes for the noted event data objects, thus decreasing the need for performing predictive data analysis operations on event data objects again after failed initial attempts to perform predictive data analysis operations on event data objects. This in turn decreases the operational load on predictive data analysis frameworks that are configured to perform predictive data analysis operations on event data objects and increases the computational efficiency as well as the operational reliability of the noted predictive data analysis frameworks. In this way, various embodiments of the present invention make important technical contributions to the fields of predictive data analysis and event processing.

CONCLUSION

Although an example processing system has been described above, implementations of the subject matter and the functional operations described herein can be implemented in other types of digital electronic circuitry, or in computer software, firmware, or hardware, including the structures disclosed in this specification and their structural equivalents, or in combinations of one or more of them.

Embodiments of the subject matter and the operations described herein can be implemented in digital electronic circuitry, or in computer software, firmware, or hardware, including the structures disclosed in this specification and their structural equivalents, or in combinations of one or more of them. Embodiments of the subject matter described herein can be implemented as one or more computer programs, i.e., one or more modules of computer program instructions, encoded on computer storage medium for execution by, or to control the operation of, information/data processing apparatus. Alternatively, or in addition, the program instructions can be encoded on an artificially-generated propagated signal, e.g., a machine-generated electrical, optical, or electromagnetic signal, which is generated to encode information/data for transmission to suitable receiver apparatus for execution by an information/data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium can also be, or be included in, one or more separate physical components or media (e.g., multiple CDs, disks, or other storage devices).

The operations described herein can be implemented as operations performed by an information/data processing apparatus on information/data stored on one or more computer-readable storage devices or received from other sources.

The term "data processing apparatus" encompasses all kinds of apparatus, devices, and machines for processing data, including by way of example a programmable processor, a computer, a system on a chip, or multiple ones, or combinations, of the foregoing. The apparatus can include special purpose logic circuitry, e.g., an FPGA (field programmable gate array) or an ASIC (application-specific integrated circuit). The apparatus can also include, in addition to hardware, code that creates an execution environment for the computer program in question, e.g., code that constitutes processor firmware, a protocol stack, a repository management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or information/data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The processes and logic flows described herein can be performed by one or more programmable processors executing one or more computer programs to perform actions by operating on input information/data and generating output. Processors suitable for the execution of a computer program include, by way of example, both general and special purpose microprocessors, and any one or more processors of any kind of digital computer. Generally, a processor will receive instructions and information/data from a read-only memory or a random access memory or both. The essential elements of a computer are a processor for performing actions in accordance with instructions and one or more memory devices for storing instructions and data. Generally, a computer will also include, or be operatively coupled to receive information/data from or transfer information/data to, or both, one or more mass storage devices for storing data, e.g., magnetic, magneto-optical disks, or optical disks. However, a computer need not have such devices. Devices suitable for storing computer program instructions and information/data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

To provide for interaction with a user, embodiments of the subject matter described herein can be implemented on a computer having a display device, e.g., a CRT (cathode ray tube) or LCD (liquid crystal display) monitor, for displaying information/data to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

Embodiments of the subject matter described herein can be implemented in a computing system that includes a back-end component, e.g., as an information/data server, or that includes a middleware component, e.g., an application server, or that includes a front-end component, e.g., a client computer having a graphical user interface or a web browser through which a user can interact with an implementation of the subject matter described herein, or any combination of one or more such back-end, middleware, or front-end components. The components of the system can be interconnected by any form or medium of digital information/data communication, e.g., a communication network. Examples of communication networks include a local area network ("LAN") and a wide area network ("WAN"), an inter-network (e.g., the Internet), and peer-to-peer networks (e.g., ad hoc peer-to-peer networks).

The computing system can include clients and servers. A client and server are generally remote from each other and typically interact through a communication network. The relationship of client and server arises by virtue of computer programs running on the respective computers and having a client-server relationship to each other. In some embodiments, a server transmits information/data (e.g., an HTML page) to a client device (e.g., for purposes of displaying information/data to and receiving user input from a user interacting with the client device). Information/data generated at the client device (e.g., a result of the user interaction) can be received from the client device at the server.

While this specification contains many specific implementation details, these should not be construed as limitations on the scope of any disclosures or of what may be claimed, but rather as descriptions of features specific to particular embodiments of particular disclosures. Certain features that are described herein in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

Thus, particular embodiments of the subject matter have been described. Other embodiments are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous.

What is claimed is:

1. An apparatus for determining a predicted risk-aware complexity determination for an event data object, the apparatus comprising one or more processors and at least one memory having computer-coded instructions stored thereon that, in execution with the one or more processors, cause the apparatus to:

identify a plurality of augmented event codes for the event data object;

for each augmented event code:
- determine a code-wise risk score that describes a measure of contribution of the augmented event code to an event complexity of the event data object, and
- determine a code-wise complexity designation that describes whether the augmented event code is associated with a predefined complexity category;

determine a risk-based complexity score for the event data object, wherein: (i) the risk-based complexity score is determined based at least in part on each code-wise risk score for an intensive risk subset of the plurality of augmented event codes, and (ii) the intensive risk subset is determined based at least in part on each code-wise risk score for the plurality of augmented event codes;

determine a category-based complexity score for the event data object based at least in part on each code-wise complexity designation for the plurality of augmented event codes;

generate the predicted risk-aware complexity determination based at least in part on the risk-based complexity score and the category-based complexity score; and perform one or more prediction-based actions based at least in part on the predicted risk-aware complexity determination.

2. The apparatus of claim 1, wherein the plurality of augmented event codes comprises one or more primary event codes associated with a primary service encoding for the event data object.

3. The apparatus of claim 1, wherein the plurality of augmented event codes comprises one or more historical event codes associated with a participant history profile for the event data object.

4. The apparatus of claim 3, wherein the one or more historical event codes comprise each event code associated with the participant history profile.

5. The apparatus of claim 3, wherein the one or more historical event codes comprise a selected subset of event codes associated with the participant history profile that are also associated with a selected time interval for the event data object.

6. The apparatus of claim 3, wherein the one or more historical event codes comprise each event code associated with the participant history profile that are also associated with a subject matter designation of the event data object.

7. The apparatus of claim 1, wherein the intensive risk subset comprises a defined-size subset of the plurality of augmented event codes having highest category-based complexity scores among the plurality of augmented event codes.

8. The apparatus of claim 1, wherein to determine the category-based complexity score, the apparatus is caused to:
- determine a selected subset of the plurality of augmented event codes having affirmative code-wise complexity designations;
- determine a size of the selected subset; and
- determine the category-based complexity score based at least in part on whether the size satisfies a size threshold.

9. The apparatus of claim 1, wherein the event data object fails to satisfy one or more initial complexity conditions.

10. A computer-implemented method for determining a predicted risk-aware complexity determination for an event data object, the computer-implemented method comprising:
- identifying, using one or more processors, a plurality of augmented event codes for the event data object;
- for each augmented event code:
  - determining, using the one or more processors, a code-wise risk score that describes a measure of contribution of the augmented event code to an event complexity of the event data object, and
  - determining, using the one or more processors, a code-wise complexity designation that describes whether the augmented event code is associated with a predefined complexity category;
- determining, using the one or more processors, a risk-based complexity score for the event data object, wherein: (i) the risk-based complexity score is determined based at least in part on each code-wise risk score for an intensive risk subset of the plurality of augmented event codes, and (ii) the intensive risk subset is determined based at least in part on each code-wise risk score for the plurality of augmented event codes;
- determining, using the one or more processors, a category-based complexity score for the event data object based at least in part on each code-wise complexity designation for the plurality of augmented event codes;
- generating the predicted risk-aware complexity determination based at least in part on the risk-based complexity score and the category-based complexity score; and
- performing one or more prediction-based actions based at least in part on the predicted risk-aware complexity determination.

11. The computer-implemented method of claim 10, wherein the plurality of augmented event codes comprises one or more primary event codes associated with a primary service encoding for the event data object.

12. The computer-implemented method of claim 10, wherein the plurality of augmented event codes comprises one or more historical event codes associated with a participant history profile for the event data object.

13. The computer-implemented method of claim 12, wherein the one or more historical event codes comprise each event code associated with the participant history profile.

14. The computer-implemented method of claim 12, wherein the one or more historical event codes comprise a selected subset of event codes associated with the participant history profile that are also associated with a selected time interval for the event data object.

15. The computer-implemented method of claim 12, wherein the one or more historical event codes comprise each event code associated with the participant history profile that are also associated with a subject matter designation of the event data object.

16. The computer-implemented method of claim 10, wherein the intensive risk subset comprises a defined-size subset of the plurality of augmented event codes having highest category-based complexity scores among the plurality of augmented event codes.

17. The computer-implemented method of claim 10, wherein determining the category-based complexity score comprises:
- determining a selected subset of the plurality of augmented event codes having affirmative code-wise complexity designations;
- determining a size of the selected subset; and
- determining the category-based complexity score based at least in part on whether the size satisfies a size threshold.

18. The computer-implemented method of claim 10, wherein the event data object fails to satisfy one or more initial complexity conditions.

19. A computer program product for determining a predicted risk-aware complexity determination for an event data object, the computer program product comprising at least one non-transitory computer-readable storage medium having computer program code stored thereon that, in execution with one or more processors, is configured for:
- identifying, using one or more processors, a plurality of augmented event codes for the event data object;
- for each augmented event code:
  - determining, using the one or more processors, a code-wise risk score that describes a measure of contribution of the augmented event code to an event complexity of the event data object, and
  - determining, using the one or more processors, a code-wise complexity designation that describes whether the augmented event code is associated with a predefined complexity category;
- determining, using the one or more processors, a risk-based complexity score for the event data object, wherein: (i) the risk-based complexity score is determined based at least in part on each code-wise risk score for an intensive risk subset of the plurality of augmented event codes, and (ii) the intensive risk subset is determined based at least in part on each code-wise risk score for the plurality of augmented event codes;
- determining, using the one or more processors, a category-based complexity score for the event data object based at least in part on each code-wise complexity designation for the plurality of augmented event codes;
- generating the predicted risk-aware complexity determination based at least in part on the risk-based complexity score and the category-based complexity score; and
- performing one or more prediction-based actions based at least in part on the predicted risk-aware complexity determination.

20. The computer program product of claim 19, wherein determining the category-based complexity score comprises:
- determining a selected subset of the plurality of augmented event codes having affirmative code-wise complexity designations;
- determining a size of the selected subset; and
- determining the category-based complexity score based at least in part on whether the size satisfies a size threshold.

* * * * *